US012447264B2

(12) United States Patent
Endyk

(10) Patent No.: US 12,447,264 B2
(45) Date of Patent: Oct. 21, 2025

(54) STERILE TRANSFER OF FLUID

(71) Applicant: TS Medical, LLC, Morrison, CO (US)

(72) Inventor: Tim Endyk, Morrison, CO (US)

(73) Assignee: TS Medical, LLC, Morrison, CO (US)

( * ) Notice: Subject to any disclaimer, the term of this patent is extended or adjusted under 35 U.S.C. 154(b) by 29 days.

(21) Appl. No.: 18/369,513

(22) Filed: Sep. 18, 2023

(65) Prior Publication Data

US 2024/0082480 A1 Mar. 14, 2024

Related U.S. Application Data

(63) Continuation of application No. 17/408,783, filed on Aug. 23, 2021, now Pat. No. 11,793,927, which is a continuation of application No. 16/740,624, filed on Jan. 13, 2020, now Pat. No. 11,097,047, which is a continuation of application No. 15/927,722, filed on Mar. 21, 2018, now Pat. No. 10,549,026, which is a continuation of application No. 14/776,868, filed as application No. PCT/US2014/026519 on Mar. 13, 2014, now abandoned.

(60) Provisional application No. 61/921,854, filed on Dec. 30, 2013, provisional application No. 61/866,346, filed on Aug. 15, 2013, provisional application No. 61/790,331, filed on Mar. 15, 2013.

(51) Int. Cl.
*A61M 5/00* (2006.01)
*A61M 5/178* (2006.01)

(52) U.S. Cl.
CPC .......... *A61M 5/008* (2013.01); *A61M 5/1782* (2013.01)

(58) Field of Classification Search
CPC ...... A61J 1/2089; A61J 1/2096; A61M 5/001; A61M 5/008; A61M 5/1782
USPC .... 211/65, 66, 69.1, 70.6, 85.13; 248/205.1, 248/220.21, 225.11, 226.11, 231.71; 206/363, 364, 365, 366; 604/411, 412, 604/413, 414
See application file for complete search history.

(56) References Cited

U.S. PATENT DOCUMENTS 1,516,795 A 11/1924 Louise
2,463,400 A * 3/1949 Lowe ...................... A61M 5/00 5/503.1
2,677,372 A 5/1954 Barnish, Jr. et al.
3,063,449 A 11/1962 Schultz et al.
(Continued)

FOREIGN PATENT DOCUMENTS

EP 0790063 B1 10/2002

OTHER PUBLICATIONS

International Search Report and Written Opinion, PCT/US2014/026519, dated Jul. 24, 2014, 7 pgs.

*Primary Examiner* — Joshua E Rodden
(74) *Attorney, Agent, or Firm* — Polsinelli PC

(57) ABSTRACT

A syringe rack securable to a surface of a fixture and configured for facilitating a sterile transfer of fluid from a non-sterile environment to a sterile environment. The syringe rack includes a securing portion and a syringe-receiving station. The syringe-receiving portion is coupled to the securing portion and configured to receive the syringe in a selectively releasable coupling arrangement where the syringe is oriented such that an opening in a barrel of a syringe projects away from the fixture when the syringe is received by the syringe-receiving station and when the securing portion is secured to the surface of the fixture.

10 Claims, 17 Drawing Sheets

(56) References Cited

U.S. PATENT DOCUMENTS

| | | | | |
|---|---|---|---|---|
| 3,567,038 | A * | 3/1971 | Ammann | A47F 5/0068 248/231.71 |
| 3,833,030 | A | 9/1974 | Waldbauer, Jr. et al. | |
| 3,853,158 | A | 12/1974 | Whitty | |
| 3,871,137 | A | 3/1975 | Grammatico | |
| 3,875,979 | A | 4/1975 | Hults | |
| 4,316,558 | A | 2/1982 | Kubiak | |
| D297,053 | S | 8/1988 | Janzen | |
| 4,846,803 | A * | 7/1989 | Emerson | A61M 5/3213 248/231.71 |
| 5,115,816 | A | 5/1992 | Lee | |
| 5,133,454 | A | 7/1992 | Hammer | |
| 5,247,972 | A | 9/1993 | Tetreault | |
| 5,255,799 | A | 10/1993 | Haynes | |
| 5,487,738 | A | 1/1996 | Sciulli | |
| 5,531,702 | A | 7/1996 | Baker et al. | |
| 5,620,422 | A | 4/1997 | Halbich | |
| 5,624,412 | A | 4/1997 | Weekley | |
| 5,814,023 | A | 9/1998 | Fulk et al. | |
| 5,873,859 | A | 2/1999 | Muntz | |
| 6,955,259 | B1 | 10/2005 | Jesse | |
| 7,458,551 | B2 | 12/2008 | Wang et al. | |
| 7,571,747 | B2 | 8/2009 | Spitz | |
| 7,681,606 | B2 | 3/2010 | Khan et al. | |
| D622,377 | S | 8/2010 | Jackson | |
| 8,286,671 | B1 | 10/2012 | Strangis | |
| 8,672,881 | B2 | 3/2014 | Nagamatsu | |
| D710,994 | S | 8/2014 | Yazbeck | |
| 9,642,778 | B1 | 5/2017 | Yazbeck | |
| 10,350,141 | B2 | 7/2019 | Metz | |
| 10,549,026 | B2 | 2/2020 | Endyk | |
| 10,661,279 | B2 | 5/2020 | Demsia | |
| 11,491,083 | B2 | 11/2022 | Colgan | |
| 2003/0024891 | A1 | 2/2003 | Diamond | |
| 2004/0144903 | A1 | 7/2004 | Cherubini et al. | |
| 2008/0065024 | A1 | 3/2008 | Witte | |
| 2008/0255520 | A1 | 10/2008 | Henderson | |
| 2012/0012719 | A1 | 1/2012 | Manke et al. | |
| 2013/0001180 | A1 | 1/2013 | Stout et al. | |
| 2013/0200023 | A1 | 8/2013 | Brotzman et al. | |

* cited by examiner

STERILE TRANSFER OF FLUID

CROSS REFERENCE TO RELATED APPLICATIONS

The present application is a continuation of and claims benefit of priority to U.S. patent application Ser. No. 17/408,783, filed Aug. 23, 2021 and entitled "Sterile Transfer of Fluid," which is a continuation U.S. patent application Ser. No. 16/740,624, filed Jan. 13, 2020 and entitled "Sterile Transfer of Fluid," which is a continuation of U.S. patent application Ser. No. 15/927,722 filed Mar. 21, 2018 and entitled "Sterile Transfer of Fluid," which is a continuation of U.S. patent application Ser. No. 14/776,868, filed on Sep. 15, 2015 and entitled "Sterile Transfer of Fluid," which is a National Stage application of International Patent Corporation Treaty Patent Application No. PCT/US2014/026519, filed Mar. 13, 2014 and entitled "Sterile Transfer of Fluid." International Patent Corporation Treaty Patent Application No. PCT/US2014/026519 claims priority under 35 U.S.C. § 119 to U.S. Provisional Patent Application 61/790,331, which was filed Mar. 15, 2013, entitled "Sterile Transfer of Fluid." International Patent Corporation Treaty Patent Application No. PCT/US2014/026519 further claims priority under 35 U.S.C. § 119 to U.S. Provisional Patent Application 61/866,346, which was filed Aug. 15, 2013, entitled "Sterile Transfer of Fluid." International Patent Corporation Treaty Patent Application No. PCT/US2014/026519 further claims priority under 35 U.S.C. § 119 to U.S. Provisional Patent Application 61/921,854, which was filed Dec. 30, 2013, entitled "Sterile Transfer of Fluid." Each of these applications is incorporated by reference in its entirety herein.

TECHNICAL FIELD

Aspects of the present disclosure involve a sterile transfer of fluid, and, more particularly, involve a syringe rack facilitating a sterile transfer of fluid.

BACKGROUND

Currently in the medical field, both in the emergency department and in the operating room, many medical personnel place themselves in harm's way in transferring a fluid (e.g., medicine) from a non-sterile environment to a sterile environment. Medical personnel conventionally utilize one the following options for transferring fluid.

One process for transferring fluid involves a non-sterile medical individual (e.g., a nurse) holding a medical vial for a sterile medical individual (e.g., a surgical assistant or technician) to attempt to thread a needle into the vial to extract the fluid into a syringe. This process often involves a significant risk of a parental stick. Further, this process increases the time spent away from various tasks, such as aiding in the surgical procedure. Additionally, this process increases the risk of contaminating the sterile environment (e.g., an operating table, sterile personnel, sterile equipment and tools, etc.), and increases the exposure time for the patient, which may increase, for example, the risk of infection.

Another process similarly involves a significant risk of parental stick. The second process involves the non-sterile individual extracting the fluid from the vial into a first syringe. The non-sterile individual then attempts to transfer the fluid from the first syringe into a second syringe held by the sterile individual by threading the needle of the first syringe through a small opening in the second syringe. This process often results in contamination of the sterile individual due to a parental stick. Further, this process increases time away from various tasks to re-sterilize, and increases the exposure time for the patient, which may increase, for example, the risk of infection.

Yet another process involves the non-sterile individual extracting the fluid into a syringe and inserting into a sterile glass from which the fluid may be extracted for use in the sterile environment. This process often results in contamination while transferring the fluid from the syringe to the glass. Further, there is a significant risk of the glass spilling, which may be detrimental to a patient who then has to wait longer for needed medication.

It is with these observations in mind, among others, that various aspects of the present disclosure were conceived and developed.

SUMMARY

Embodiments described and claimed herein address the foregoing problems, among others, by providing a medical rack for fast and easy transfer of fluid from a non-sterile environment to a sterile environment.

Disclosed herein is a medical rack securable to a surface of a fixture and configured for transferring fluid from a non-sterile environment to a sterile environment that includes a syringe having a tab extending radially from a barrel of the syringe, an opening at a distal end of the barrel, and a plunger extending from a proximal end of the barrel.

In one embodiment, the medical rack includes a securing portion and a syringe-receiving station. The securing portion is configured for selectively releasable securing to the surface of the fixture. The syringe-receiving station is coupled to the securing portion and configured to receive the syringe in a selectively releasable coupling arrangement where the syringe is oriented such that the opening projects away from the fixture when the syringe is received by the syringe-receiving station and the securing portion is secured to the surface of the fixture.

In one version of the embodiment, the medical rack is be so configured such that the plunger can be proximally extended without contacting the fixture when the syringe is received by the syringe-receiving station and the securing portion is secured to the surface of the fixture. In another version of the embodiment, the syringe-receiving station is coupled to the securing portion via a selectively removable configuration. In yet another version of the embodiment, the syringe-receiving portion includes a lock that prevents lateral escape of the syringe from the syringe-receiving station. This version also includes where the lock is adapted to rotationally engage the tab of the barrel of the syringe. In another version of the embodiment, the syringe-receiving station includes upper and lower elements that are vertically spaced-apart from each other, where the upper and lower elements each configured for selectively releasable coupling with the syringe. The version may further include wherein the upper element is configured to inhibit lateral displacement of the syringe when coupled to the syringe, and the lower element is configured to inhibit both lateral and longitudinal displacement of the syringe when coupled to the syringe. The version may further include one of the upper or lower elements configured to inhibit at least lateral displacement of the syringe when coupled to the syringe, and the other of upper or lower elements is configured to inhibit at least longitudinal displacement of the syringe when coupled to the syringe. The version may also include wherein the other of the upper and lower elements is further configured to inhibit both longitudinal and lateral displacement of the syringe when coupled to the syringe. Further still, the version may include wherein the upper element receives the barrel near the distal end, and the lower element receives the tab.

In one version of the embodiment, the upper element includes a syringe-receiving recess that is vertically aligned with the lower element, which includes a syringe-receiving space. This version may also include wherein the syringe-receiving recess is configured to receive therein the barrel near the distal end, and the syringe-receiving space is configured to receive the barrel near the proximal end. Further, this version may include wherein the syringe-receiving space is further configured to receive the tab. And, this version may include wherein the syringe-receiving space defines a slot perpendicular to a longitudinal axis of the syringe-receiving station, the slot being configured to receiving therein the tab. In this version, the syringe-receiving recess includes a configuration that results in the barrel snapping into place within the syringe-receiving space.

Also disclosed herein is a method of employing the embodiment of the medical rack described above for transferring fluid from the non-sterile to the sterile environment. In one embodiment, the method includes loading the syringe with the fluid from the non-sterile environment while the syringe is received by the syringe-receiving station such that the opening projects away from the fixture when the syringe is received by the syringe-receiving station and the securing portion is secured to the surface of the fixture.

In one version of the embodiment, the non-sterile environment includes a non-sterile syringe containing the fluid, the non-sterile syringe configured to couple with the syringe via a butterfly tip in order to transfer the fluid. The version may also include coupling the non-sterile syringe to the syringe via the butterfly tip prior to loading the syringe with the fluid. In still other versions of the embodiment, the method may include various features of the medical rack as described above with respect to the various embodiments.

Other embodiments are also described and recited herein. Further, while multiple embodiments are disclosed, still other embodiments of the presently disclosed technology will become apparent to those skilled in the art from the following detailed description, which shows and describes illustrative embodiments of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

DETAILED DESCRIPTION

Aspects of the present disclosure involve systems, apparatuses, and methods for transferring a fluid from a non-sterile environment to a sterile environment. Generally, a medical rack adapted to securely hold one or more syringes in a sterile environment is provided. The medical rack frees medical personal to perform other activities, including attending to a surgeon or other sterile personnel during procedures, thereby decreasing patient exposure time to any contaminants that may be present. Further, the medical rack provides for quick and easy transfer of fluids while substantially decreasing the risk of contaminating the sterile environment or of parental stick. The medical rack may be made from a variety of robust materials that may be used in a sterile environment, including, without limitation, stainless steel, polymers, and a strong and durable grade plastic. In one embodiment, the rack is made from a transparent material (e.g., acrylic). In another embodiment, the entire rack includes a single disposable or reusable unit. In another embodiment, the rack includes detachable components, some or all of which are disposable. The rack may be included in a sterile kit, loaded with various syringes. The rack may be sterilely stocked and packaged upon receiving and then discarded or sterilized once finished.

The medical rack may be adapted to hold a variety of syringe types and sizes, as well as other devices adapted to extract or otherwise transfer fluid. The angle of the rack can be modified and adapted to fit any angle. In various aspects of the present disclosure, each of the syringes is conventional in construction and operation. Thus, the syringe includes a barrel that receives fluid to be administered. A butterfly tip, hollow needle, or stopper may be secured to one end of the barrel by a hub and is coupled in fluid communication with the interior of the barrel. The end of the barrel, remote from the needle, may be provided with a radially extending tab, which is typically engaged by the fingers of a medical user operating the syringe. The syringe further includes a plunger adapted for axial movement within the barrel. The plunger extends to a piston which forms a fluid tight seal with the interior surface of the barrel. The end of the plunger, remote from the piston, may be provided with a plate which is typically engaged by the thumb of an individual operating the syringe. However, it will be appreciated that the medical rack may be adapted to hold other embodiments of a syringe, other medical equipment or tools, and/or other devices adapted to transfer fluid.

Figure 1:
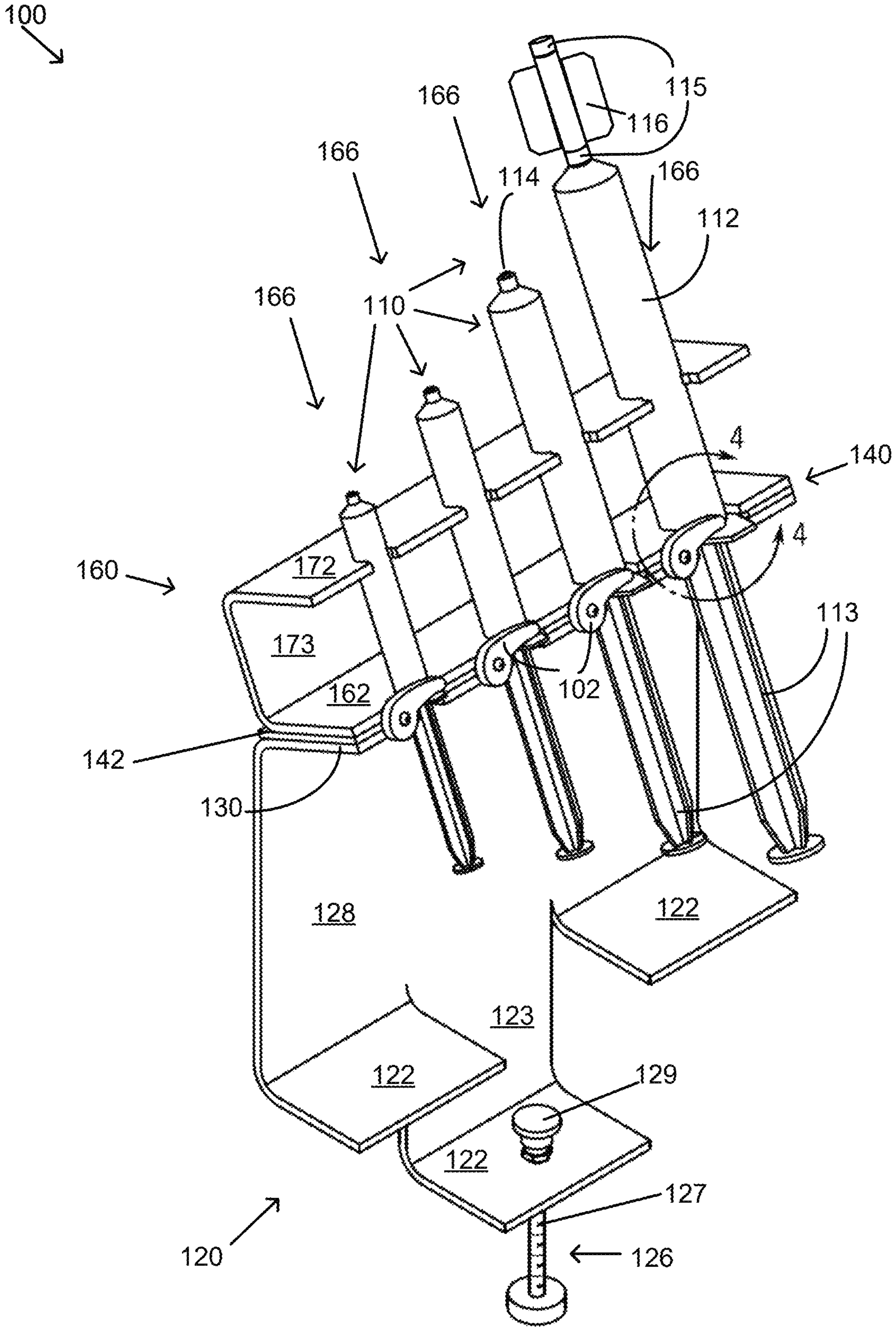
FIG. 1 shows an isometric front view of an example medical rack holding syringes.

Referring to the embodiment in FIG. 1, the medical rack 100 includes a securing portion 120, a receiving portion 160, and a tab engaging portion 140 between the securing portion 120 and the receiving portion 160. The receiving portion 160, in combination with the tab engaging portion 140, is configured to receive one or more syringes 110 in manner that allows the syringes 110 to be supported on the rack 100. The securing portion 120 includes one or more securing members 122 adapted to engage a fixture 124, such as a medical table or tray, thereby facilitating the rack 100 being fixed to and supported off of the fixture 124. A clamp 126 or similar securing mechanism secures the securing portion 120 to the fixture 124.

In the embodiment in FIG. 1, the rack 100 includes two upper securing members 122 that support the rack 100 on a top side of the fixture 124 and a single lower securing member 122 that supports the rack 100 on a bottom side of the fixture 124. The two upper securing members 122 and the single lower securing member 122 are planar, plate-like members with opposing top and bottom planar surfaces. The two upper securing members 122 are on outer ends of the rack 100, whereas the single lower securing member 122 is between the two upper securing surfaces 122. The single lower securing member 122 includes an extended section 123 that extends the single lower securing member 122 from a junction with the two upper securing members 122 downward and beneath a portion of the fixture 124, as can be understood from FIG. 3.

Figure 3:
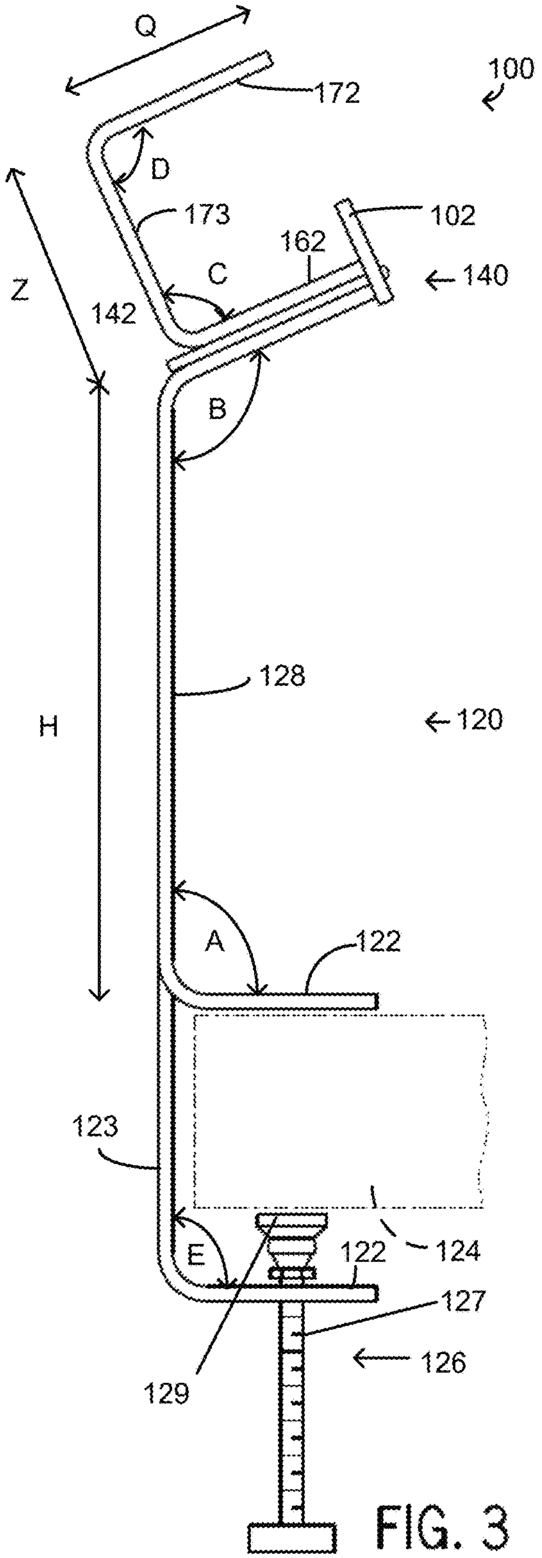
FIG. 3 shows a side view of the medical rack coupled with a fixture (broken line).

Referring to the single lower securing member 122, as seen in FIG. 1, the clamp 126 includes a swivel head 129 on an adjusting screw 127 that communicates through the single lower member 122 on the bottom portion of the securing portion 120. The adjusting screw 127 can be adjusted to secure the swivel head 129 against a bottom surface of the fixture 124, as illustrated in FIG. 3. While a clamp 126 with a swivel head 129 and an adjusting screw 127 are described in reference to the embodiment in FIG. 1, various other securing mechanisms are possible and within the scope of the present disclosure. For example, a quick-release bar clamp can be utilized in place of the clamp 126 illustrated in the embodiment of FIG. 1.

Figure 2:
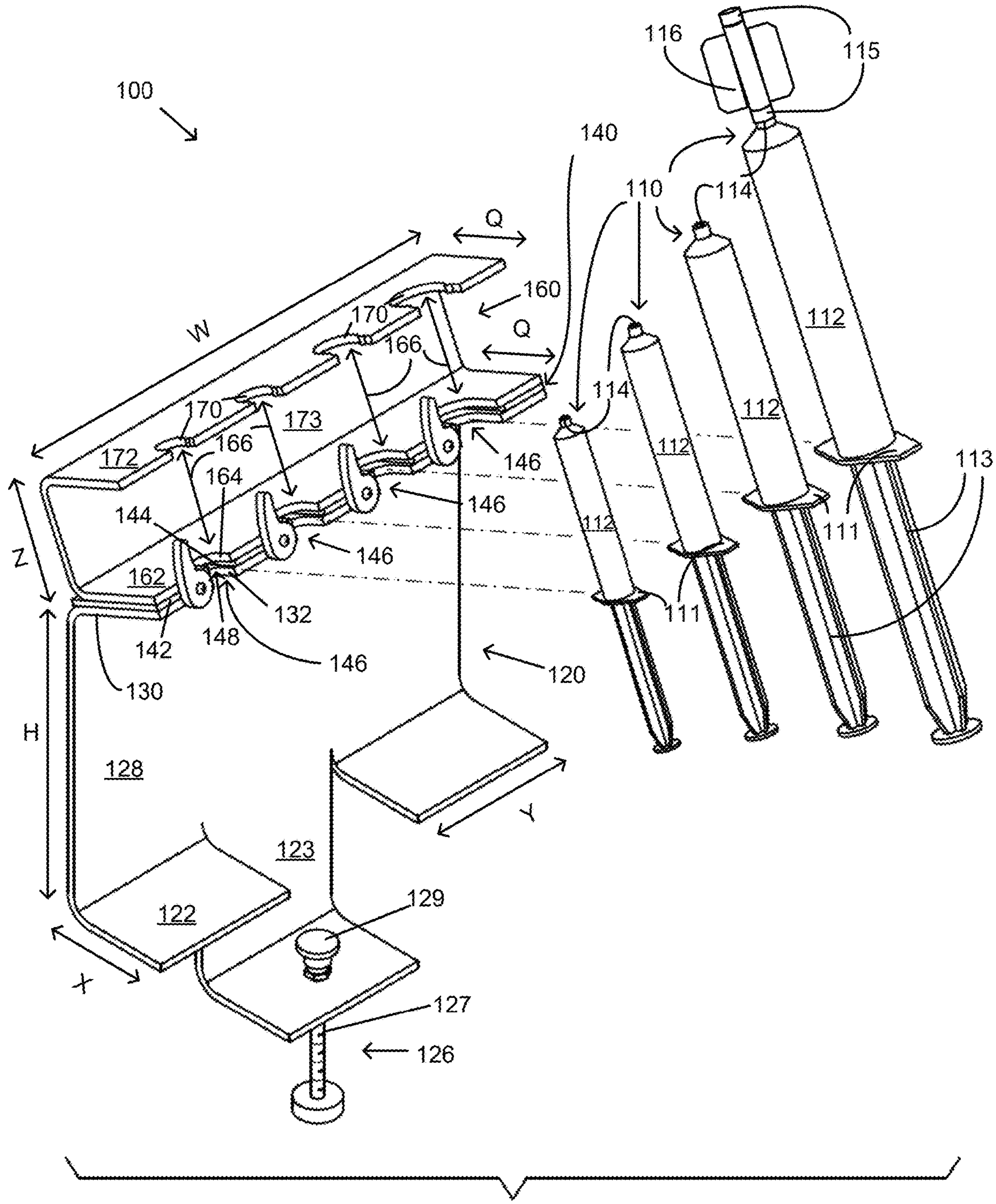
FIG. 2 shows an isometric front view of the medical rack not holding the syringes.

As can be understood from FIGS. 1-3, the medical rack 100 is adapted to releasably support the positioning of a variety of syringes 110 in an orientation that angles an opening 114 in the barrel 112 of the syringe 110 outward and away from the fixture 124. In particular, as seen in FIGS. 2-3, the securing portion 120 further includes a positioning section 128 extending from the one or more securing members 122. The positioning section 128 is an elongated, planar, and plate-like member that extends upward and away from securing members 122 and the fixture 124 a sufficient distance to allow for the plunger shaft 113 of the syringe 110 to be extended outward from the barrel 112 without interference by the fixture 124. The positioning section 128 extends from the one or more securing members 122 at an angle A, which can include multiple angles, as will be discussed below.

As shown in FIGS. 1-3, in some embodiments, the tab engaging portion 140 of the rack 100 may be formed via a sandwiched configuration made up of an upper element 130 of the securing portion 120, an intermediate portion (e.g., the below discussed tab-engaging member 142), and a lower element 162 of the receiving portion 160. In other embodiments, the sandwiched configuration of the tab engaging portion 140 of the rack 100 may be made up of different combinations of the securing portion 120, the receiving portion 160, and/or other portions that are separate elements from the either or both of the portions 120, 140. Further, while the tab engaging portion 140 of the rack 100 is configured via the combination of the below-discussed sandwiched recesses 132, 144, 164 and resulting syringe-receiving spaces 146 and tab-receiving channels 148 that receive syringe barrels 112 and tabs 111 in a manner that prevents the syringes 110 from laterally and longitudinally displacing when received in said spaces 146 and channels 148, the rack 100 and associated methods disclosed herein also encompass any means or methods of engaging and supporting syringes 110 on the rack 100 in the orientation and manner disclosed herein that facilitates the fluid filling methods disclosed herein.

Referring to a top portion of the securing portion 120, and referring to FIGS. 1-2, a lower engaging member 130 of the tab engaging portion 140 extends outward from the positioning section 128 in the same general direction as the one or more securing members 122. In addition to being the lower engaging member 130 of the tab engaging portion 140 that interacts with the syringes 110, the member 130 is also a planar, plate-like member that is a part of the securing portion 120 of the rack 100. In this and other embodiments, the securing members 122, the positioning section 128, and the lower engaging member 130 of the securing portion 120 may be generally planar members having generally smooth planar surfaces and may be unitarily formed from a single piece of material.

Turning now to various angular relations between respective portions of the rack 100, as can be understood from FIGS. 1 and 3, the lower engaging member 130 of the tab engaging portion 140 extends at an angle A relative to the positioning section 128. And, an angle B is defined between a lower planar surface of the lower engaging member 130 and a front planar surface of the positioning section 128 such that the opening 114 in the barrel 112 of any syringe 110 secured in the receiving portion 160 is easily accessible for the coupling of a non-sterile syringe with the syringe 110 via a butterfly tip 116 or other coupling mechanism (e.g., needle) to transfer fluid. As seen in FIGS. 1-2, the butterfly tip 116 is a hollow, tubular coupling mechanism with dual-sided female ports 115 on opposing ends of the butterfly tip 116 that frictionally engage with respective distal, male, ends of a sterile syringe 110 in a rack 100 and a non-sterile syringe, which is held by a medical professional. By transferring fluid through the butterfly tip 116 as opposed to a needle, the risk of parental stick is eliminated.

Figure 4:
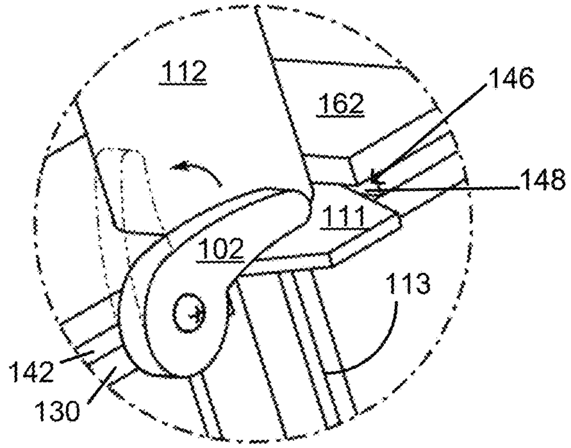
FIG. 4 shows an up-close isometric front view of a lock engaging with a radially extending tab of a syringe.
Figure 6:
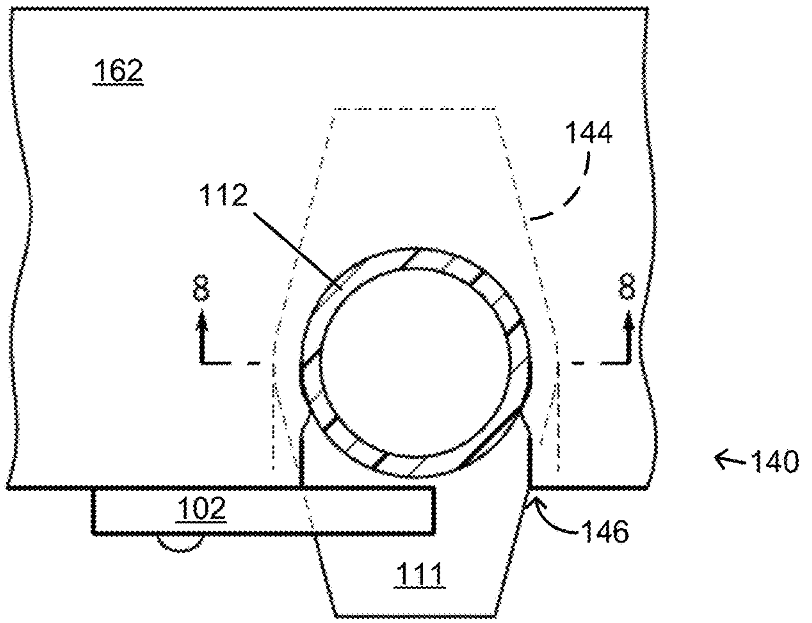
FIG. 6 shows a close-up top plan view of the syringe in a tab engaging portion of the medical rack.
Figure 9:
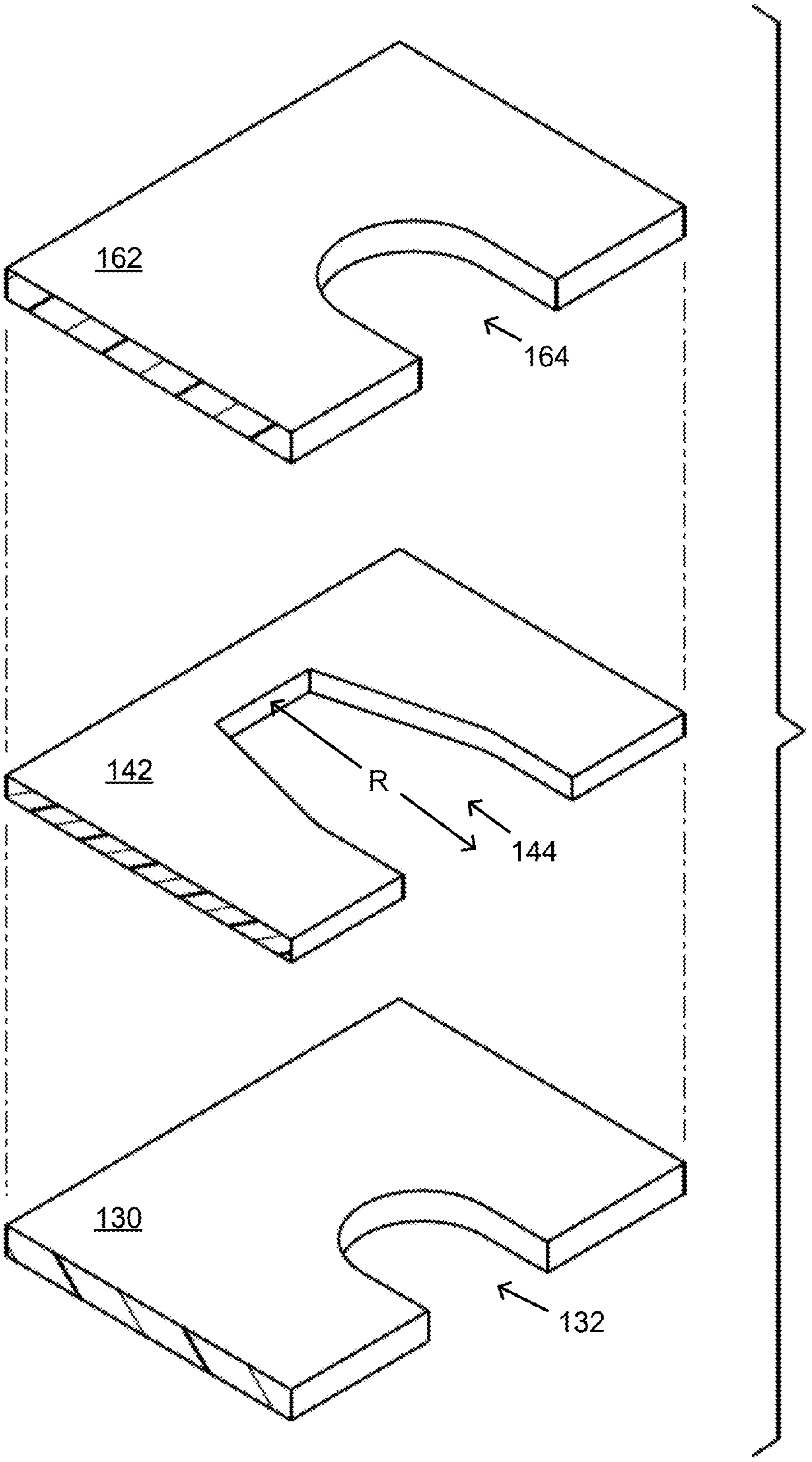
FIG. 9 shows an exploded view of the medical rack of FIG. 8.

Referring now to an additional element of the sandwich configured tab-engaging portion 140, namely, the tab engaging member 142, as seen in FIGS. 1, 2, 3 and 9, the tab engaging member 142 is a generally planar member 142 that is positioned on top of an upper planar surface of the lower engaging member 130 of the tab engaging portion 140. The tab engaging member 142 includes upper and lower planar surfaces and further includes a generally rectangular perimeter with one or more recesses 144 defined in a front outer edge of the perimeter of the tab engaging member 142, as shown in FIGS. 4, 6 and 9. Each of the recesses 144 is shaped and sized to mirror the shape and size of the radially extending tab 111 of the barrel 112 of a syringe 110, as can be understood from FIGS. 4, 6 and 9. In particular, the recesses 144 are cut outs, indentations, or notches to an otherwise straight edge of the tab engaging member 142.

As indicated in FIGS. 1, 3-5, 8 and 9, the tab engaging member 142 is disposed between the upper planar surface of the lower engaging member 130 of the tab engaging portion 140 (the tab engaging portion 140 also being part of the securing portion 120) and a lower planar surface of an upper engaging member 162 of the tab engaging portion 140 (the upper engaging member also being part of the receiving portion 160). In the present embodiment, the tab engaging member 142 is securely sandwiched between the lower engaging member 130 and the upper engaging member 162 such that the lower and upper planar surfaces of the tab engaging member 142 respectively make surface abutting contact with the upper planar surface of the lower engaging member 130 and the lower planar surface of the upper engaging member 162.

In conjunction with the one or more tab-shaped recesses 144 in the tab engaging member 142, both of the lower engaging member 130 and the upper engaging member 162 include one or more recesses 132, 164 defined in each respective outer perimeter edge. As illustrated in FIG. 9, the recesses 132, 164 may be U-shaped. In one embodiment, each of the recesses 132 in the lower engaging member 130 of the tab engaging portion 140 and each of the recesses 164 in the upper engaging member 162 of tab engaging portion 140 are positioned relative to one of the tab-receiving recesses 144 in the tab engaging member 142 of the tab engaging portion 140 so that all of the recesses are aligned to form a syringe-receiving space 146, as can be understood from FIGS. 2, 4-6, 8 and 9. Thus, the alignment of the recesses 132, 142, 162 of the syringe-receiving space 146 of the tab engaging portion 140 are such that, when a syringe 110 is received in the syringe-receiving space 146, the tab 111 of the syringe 110 is matingly received in the tab-receiving recess 142 while the barrel 112 of the syringe 110 is matingly received by the upper or barrel-receiving recess 164 and the plunger shaft 113 of the syringe 110 extends through the lower receiving recess 132 as can be understood from FIGS. 1, 2, 4-6, and 9.

Thus, the aligned recesses 164, 144, 132 form a receiving space 146 in the tab engaging portion 140 of the rack 100 for engaging with a portion of a syringe 110 that is to be mounted to the rack 100. As seen in FIGS. 2, 6, 8 and 9, the receiving space 146 in the tab engaging portion 140 of the rack 100 is formed by the collective sandwiching or stacking of the lower engaging member 130, the tab engaging member 142, and the upper engaging member 162 such that the respective perimeter edges of the members 130, 142, 162 and the recess 132, 144, 164 associated with each line up.

In one embodiment, as seen in FIG. 9, the tab-receiving recess 144 of the tab engaging member 142 of the tab engaging portion 140 of the rack 100 extends further than or deeper into its member 142 than each of the respective recesses 132, 164 of the lower engaging member 130 of the tab engaging portion 140 of the rack 100 and the upper engaging member 162 of the tab engaging portion 140 of the rack 100, thereby forming a tab-receiving channel 148 in the plane of the tab-receiving member 142 that is between the upper planar surface of the lower engaging member 130 and the lower planar surface of the upper engaging member 162, this channel 148 having lateral boundaries defined by the edges of the tab-receiving recess 144 and lower and upper boundaries respectively defined by the upper planar surface of the lower engaging member 130 and the lower planar surface of the upper engaging member 162. Being so configured, the tab-receiving channel 148 of the tab engaging portion 140 of the rack 100 is adapted to matingly receive and secure the radially extending tab 111 of the barrel 112 of a syringe 110 such that, when the syringe 110 is mounted to the rack 100 and the tab 111 is matingly received in the tab-receiving channel 148, as can be understood from FIGS. 1, 4-6, 8, and 9, the channel 148 prevents the syringe 110 from moving laterally and longitudinally.

Moving now to the top most portion of the rack 100 and as seen in the embodiment of FIGS. 1-3, the receiving portion 160 includes a generally C-shaped body that extends a width of the rack 100 and includes the upper engaging member 162 of the tab engaging portion 140 of the rack 100, a syringe barrel engaging member 172, and an adjoining member 173 that perpendicularly extends between the syringe barrel engaging member 172 and the upper engaging member 162 of the tab engaging portion 140 of the rack 100. As with other parts of the medical rack 100, each of the syringe barrel engaging member 172, upper engaging member 162 of the tab engaging portion 140, and adjoining member 173 may include planar, plate-like surfaces that are either unitarily formed together to form the unitary construction of the receiving portion 160 or coupled together to form a multi-piece receiving portion 160.

As seen in FIG. 1-3, the syringe barrel engaging member 172 and upper engaging member 162 of the tab engaging portion 140 are generally parallel and each extends generally the same distance outward from the adjoining member 173. Each of the syringe barrel engaging member 172 and upper engaging member 162 of the tab engaging portion 140 includes a front perimeter edge extending the width of the rack 100. And, as described previously, the upper engaging member 162 of the tab engaging portion 140 includes one or more recesses 164 defined in the front perimeter edge of the upper engaging member 162. Similarly, the syringe barrel engaging member 172 includes one or more recesses 170 defined in the front perimeter edge of the syringe barrel engaging member 172. Each of the recesses 170 in the syringe barrel engaging member 172 are positioned so to be aligned with the one or more recesses 164 in the upper engaging member 162 of the tab engaging portion 140. As a result, each upper syringe-receiving recess 170 of the syringe barrel engaging member 172 is aligned with a respective lower syringe-receiving space 146 of the tab engaging portion 140, as can be understood from FIG. 1.

Figure 5:
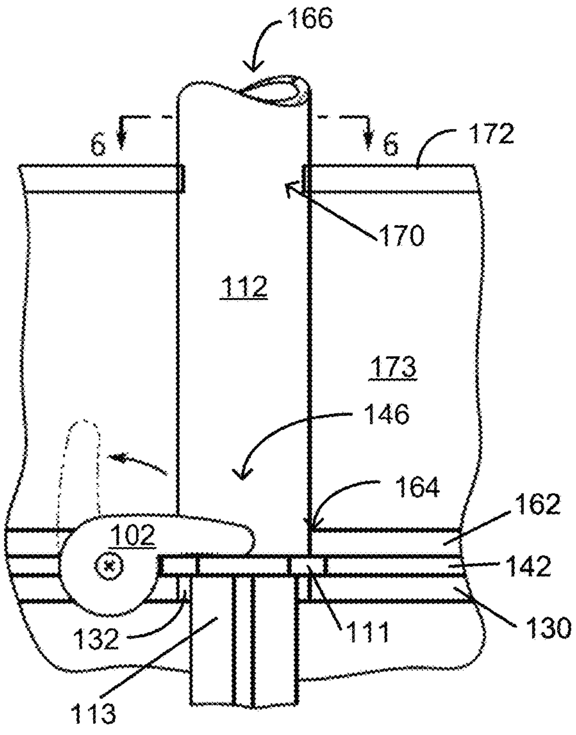
FIG. 5 shows a front view of the medical rack holding a syringe.

As can be understood from FIGS. 1 and 5, in one embodiment, the upper syringe-receiving recess 170 receives the syringe barrel 112 near the distal end of the syringe 110, and the lower syringe-receiving space 146 receives the syringe barrel 112 and syringe tab(s) 111 near the proximal region of the syringe 110. In other embodiments, the rack 100 may be configured to engage one or more syringes 110 via other structural and contact arrangements so long as the syringes 110 are oriented in a manner that facilitates the liquid transfers as disclosed herein. Thus, as shown in FIG. 2, each upper syringe-receiving recess 170 is paired with lower, aligned syringe-receiving space 146 to form a paired, vertically aligned, recessed configuration 166 that ends up being a syringe-receiving station 166 in which a single syringe 110 can be mounted on the rack 100, as illustrated in FIGS. 1 and 5.

Figure 7:
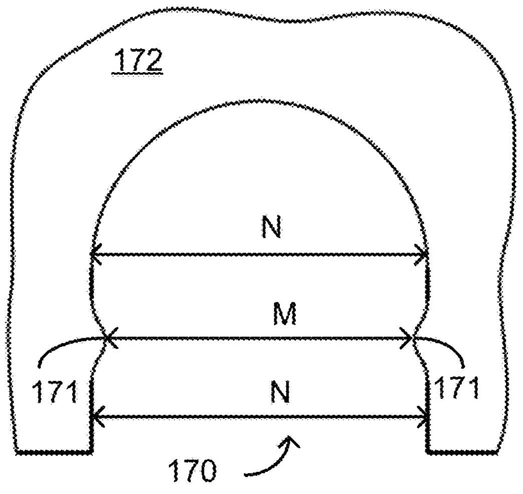
FIG. 7 shows a close-up top plan view of the receiving portion of the medical rack without the syringe.

Turning again to the upper syringe-receiving recess 170 of the syringe barrel engaging member 172, as shown in FIG. 7, the upper syringe-receiving recess 170 defines a first width M that separates a pair of second widths N. In particular, the upper syringe-receiving recess 170 includes a pair of opposed tabs 171 that extend into the recess 170 from a side edge of the recess 170. The tabs 171 can either flex or will cause a syringe barrel 112 to flex when the syringe 110 is mounted to the syringe barrel engaging member 172. Thus, the barrel 112 of the syringe 110 will "snap" into place within the upper syringe-receiving recess 170 of the syringe barrel engaging member 172 and be held in place by the tabs 171 on either side of the barrel 112. The first width M and the second width N may be sized according to a size of the barrel 112 of a syringe 110. Each of the syringe-receiving stations 166 are shaped and sized to mirror the shape and size of the various sized syringes 110 (e.g., 5 mL, 10 mL, 20 mL) received therein. More specifically, each recess 130, 142, 164, 170 forming a respective syringe-receiving station 166 is shaped and sized to mirror the shape and size of the various respective syringe elements received therein. When the syringes 110 are installed in the medical rack 100, the syringe-receiving stations 166 position the one or more syringes 110 such that an opening 114 in the barrel 112 of the syringe 110 is directed generally away from the securing portion 120 and such that the opening 114 is easily accessible for the insertion of the distal end of a non-sterile syringe into the butterfly tip 116 to transfer fluid.

Figure 8:
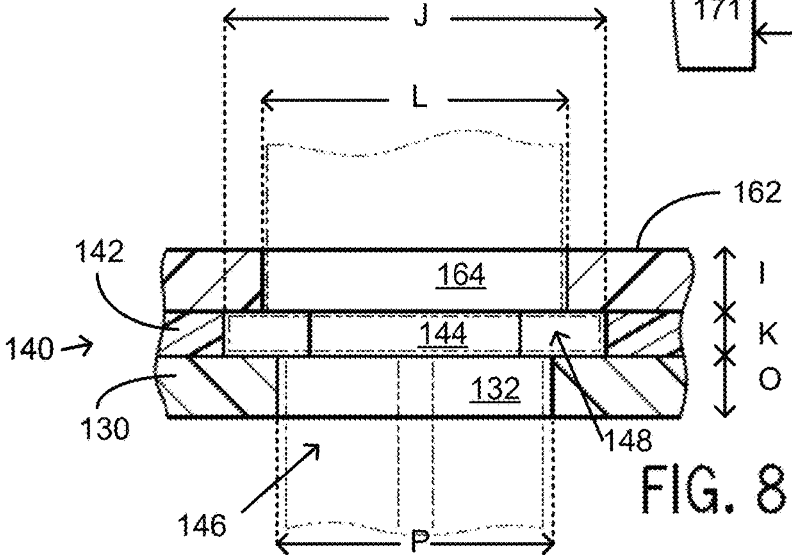
FIG. 8 shows a cross-sectional elevation view as taken along section line 8-8 in FIG. 6 of a tab engaging portion of the medical rack.

Turning again to the sandwiched arrangement of the tab engaging portion 140, as seen in FIGS. 8-9, the upper engaging member 162 of the tab engaging portion 140 defines a thickness I and the recess 164 defines a width L. The tab engaging member 142 of the tab engaging portion 140 defines a thickness k and the recess 144 defines a width J and a depth R. The lower engaging member 130 of the tab engaging portion 140 defines a thickness O and the recess 132 defines a width P. The various widths and depth depend on a particular syringe 110 that fits the particular syringe-receiving stations 166. In particular, the syringe-receiving stations 166 may be sized to fit syringes 110 of different sizes (e.g., 5 mL, 10 mL, 20 mL). Each respective size of syringe 110 can include standard sizes of tabs 111, barrel 112, etc. that can be considered in sizing the various components of the medical rack 100.

To further secure the syringes 100 within the syringe-receiving stations 166, as shown in FIGS. 4-6, the medical rack 100 includes one or more locks 102, each posited relative (e.g., generally perpendicular) to a lower syringe-receiving space 146 of the tab engaging portion 140. The locks 102 may rotate to engage the radially extending tab 111 of the barrel 112 of a syringe 110. The locks 102 can be modified and adapted in a variety of manners, including, but not limited to, slide latch, ratchet latch, lanyard pin, rubber grommet, friction fit, snap fit, etc.

The rack 100 may additionally include one or more features to further secure the syringes 110 from moving longitudinally or laterally. In certain embodiments, to further secure each of the syringes 110 from moving longitudinally or laterally, a lock (not shown) may slide horizontally to engage the extending tab of the barrel of a syringe. In another embodiment, a locking pin (not shown) attached to a lanyard may engage with a hole on the opposite side of the syringe finger tab to securely lock the syringe in place. In other embodiments, a securing cap may be horizontally rotated. A finger tab (male end) may be inserted into a receiving portion (female end) of the securing cap, encompassing the end of the finger tabs and then attached to the opposite side of the syringe. The attachment may be adapted or modified to fit a variety of methods, including but not limited to, snaps, ratchet, hitch pin, friction fit, etc. In still another embodiment, rubber grommets may be used to secure the finger tabs that have been inserted into the female receiving portion of the medical rack.

The rack 100 may additionally include one or more various fasteners for the syringes 110. In certain embodiments, rubber grommets/rubber clamps can be used for the tab engaging portion that extends further than each of the respective recesses of the members 130, 162 of the of the tab engaging portion 140, thereby forming a channel 148 adapted to receive and secure the radially extending tab 111 of the barrel 112 of a syringe 110. The channel 148 prevents the syringe from moving laterally and longitudinally. In other embodiments, a retaining clip has a receiving portion where the body of the syringe is securely held reducing or eliminating any movement laterally and longitudinally. In still other embodiments, broom spring clips/holders/clamps have a receiving portion that when the body of the syringe meets the fasteners, clamp/holder/spring clips, the fastener compresses to allow the body of the syringe in and then springs back and securely holds the syringe in place reducing or eliminating any movement laterally and longitudinally. In certain embodiments, the recess of the ball bearing engaging portion extends further than each of the respective recesses of the engaging members 130, 142, 164 of the tab engaging portion 140 and the member 172 of the receiving portion 160, thereby forming a channel 148 adapted to receive and secure the radially extending tab 111 of the barrel 112 of a syringe 110. The channel prevents the syringe from moving laterally and longitudinally.

Referring to the embodiment of FIGS. 2-3, the rack 100 may include sample dimensions as follows. A height H of the positioning section 128 is about 5 inches and a width W of the rack 100 is about 12 inches. Each of the one or more members 122 extends outward X from the positioning section 128, X being about 3 inches, and extends across the rack 100 Y, which is about 4 inches. The receiving portion 160 has a height Z of about 1.75 inches, and each of the members 130, 142, 162, 172 extends Q about 2.25 inches.

Referring to FIGS. 7-9, sample dimensions of the recess 170 are as follows: N is about 0.9 inches for a 20 mL syringe, 0.66 inches for a 10 mL syringe, or 0.58 inches for a 5 mL syringe; and M is about 0.84 inches for a 20 mL syringe, 0.62 inches for a 10 mL syringe, and 0.52 inches for a 5 mL syringe. Referring to FIG. 8, sample dimensions of the thickness of the members 130, 142, 160 are as follows: the thickness I of the member 162 is about 0.64 inches for a 10 mL syringe, about 0.84 inches for a 20 mL syringe, and about 0.53 inches for a 5 mL syringe; the thickness K of the member 142 is about 0.08 inches for a 10 mL syringe, about 0.1 inches for a 20 mL syringe, and about 0.08 inches for a 5 mL syringe; the thickness O of the member 130 is about 0.60 inches for a 10 mL syringe, about 0.76 inches for a 20 mL syringe, and about 0.49 inches for a 5 mL syringe. The width L of the recess 164 is about 0.64 inches for a 10 mL syringe, about 0.84 inches for a 20 mL syringe, and about 0.62 inches for a 5 mL syringe; the width J of the recess 142 is about 0.74 inches for a 10 mL syringe, about 0.99 inches for a 20 mL syringe, and about 0.62 inches for a 5 mL syringe; the width P of the recess 130 is about 0.6 inches for a 10 mL syringe, about 0.76 inches for a 20 mL syringe, and about 0.49 inches for a 5 mL syringe. Finally, the depth R of the recess 144 is about 1.25 inches for a 20 mL syringe, about 0.92 inches for a 10 mL syringe, and about 0.85 inches for a 5 mL syringe. These dimensions are intended to be exemplary and may include other dimensions.

Referring to the embodiment of FIGS. 2-3, the rack 100 may include sample angles as follows. The angle A between the positioning section 128 and the one or more securing members 122 is about 90 degrees. The angle B between the positioning section 128 and the engaging member 130 is about 120 degrees. An angle C between the engaging member 162 and the adjoining section 173 is about 90 degrees. Similarly, an angle D between the adjoining section 173 and the member 172 is about 90 degrees. And, an angle E between the single lower securing member 122 of the one or more upper securing members 122 and a section 123 that extends between the two upper securing members 122 and the one lower securing member 122 is about 90 degrees. These dimensions are intended to be exemplary and may include other dimensions.

Variations of the medical rack 100 can further include variations to the angles between the various components of the rack 100. For example, the positioning section 128 can extend upwards from the one or more upper securing members 122 in various angles. For example, while FIG. 3 shows the positioning section 128 extending an angle A of about 90 degrees from the one or more upper securing members 122, the positioning section 128 can extend from the one or more upper securing members 122 at angles A such as 120 degrees, 135 degrees, 150 degrees, or 180 degrees, among others.

Other variations to the medical rack 100 may include different angles B between the positioning section 128 and the lower engaging member 130 and, thus, the other members 142, 162 of the tab engaging portion 140. For example, while the embodiment of FIG. 3 shows an angle B of about 120 degrees between the positioning section 128 and the engaging member 130, the angle can be about 90 degrees, 135 degrees, 150 degrees, or 180 degrees, among others.

Figure 10:
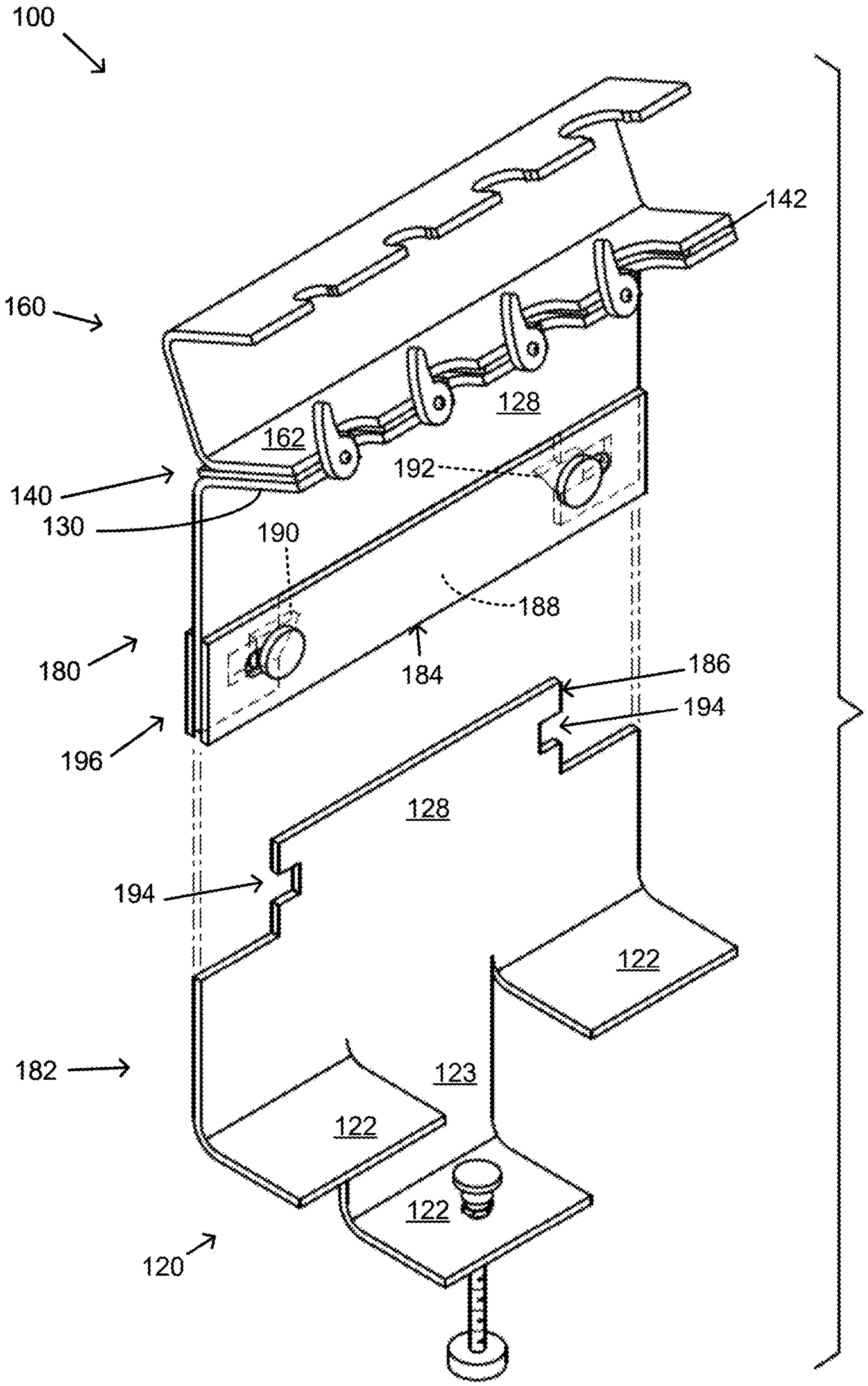
FIG. 10 shows an isometric front view of an example medical rack including a top detachable portion and a bottom detachable portion in a detached arrangement.

Turning now to an alternative embodiment of the medical rack 100, as shown in FIG. 10, the rack 100 is detachable between the engaging member 130 of the tab engaging portion 140 and the one or more upper securing members 122 of the securing portion 120. Thus, a top detachable portion 180 includes the receiving portion 160, the tab engaging portion 140, the engaging surface 130, and a top region of the positioning section 128. And, a bottom detachable portion 182 includes a bottom region of the positioning section 128 and the securing portion 120 of the rack 100. The rack 100 is detachable between the top detachable portion 180 and the bottom detachable portion 182 via an attachment mechanism 196, which will be described in detail below. The top detachable portion 180 of the rack 100 can be detached from the bottom portion 182 of the rack 100 so that the rack 100 can be properly sterilized and pre-stocked with the corresponding syringes 110.

The bottom detachable portion 182 of the rack 100 can be secured to the fixture 124, as previously described with respect to FIG. 3, by the securing portion 120. Or, the bottom detachable portion 182 can be secured to the fixture by one of a variety of securing methods described herein. It is to be understood that the various features for securing the detachable rack 100 can be modified and combined in different methods (e.g., spring loaded, manual latch, amount force needed to attach the detachable rack)

Figure 11:
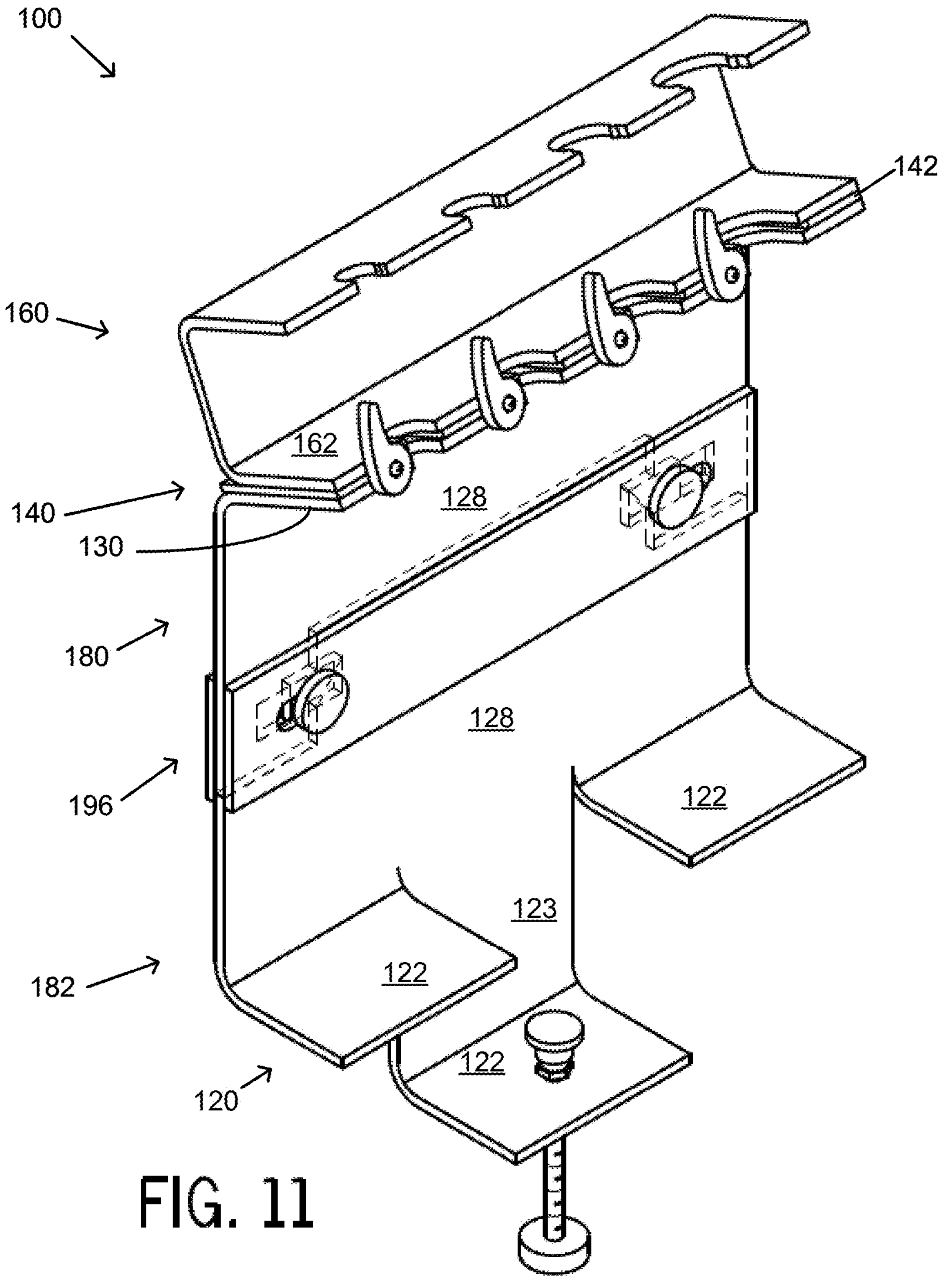
FIG. 11 shows the top detachable portion and the bottom detachable portion of the medical rack of FIG. 10 in an attached arrangement.
Figure 12:
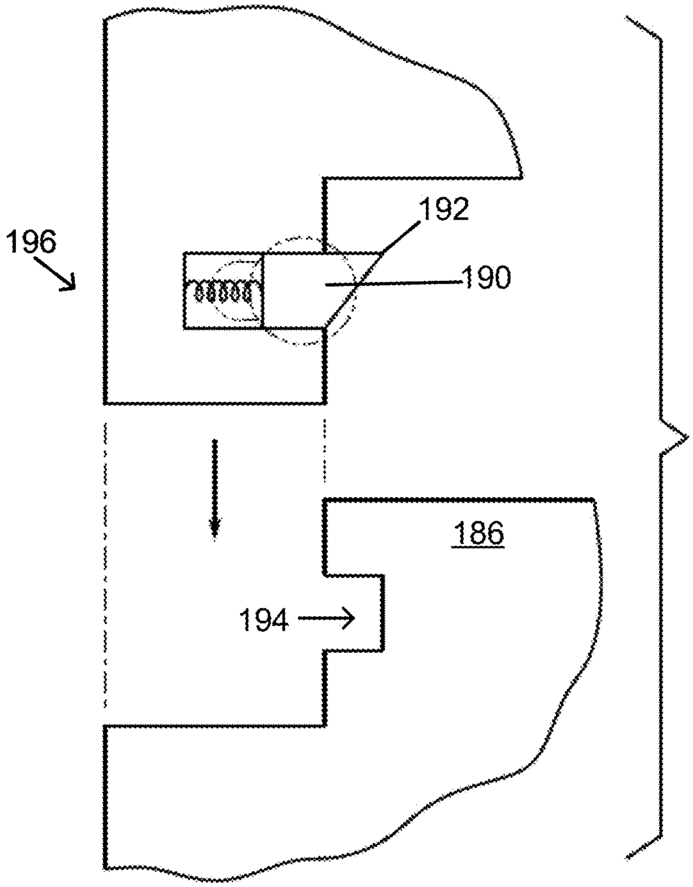
FIGS. 12-14 show a front view of an example of a portion of an attachment mechanism securing the top detachable portion to the bottom detachable portion of the medical rack.
Figure 13:
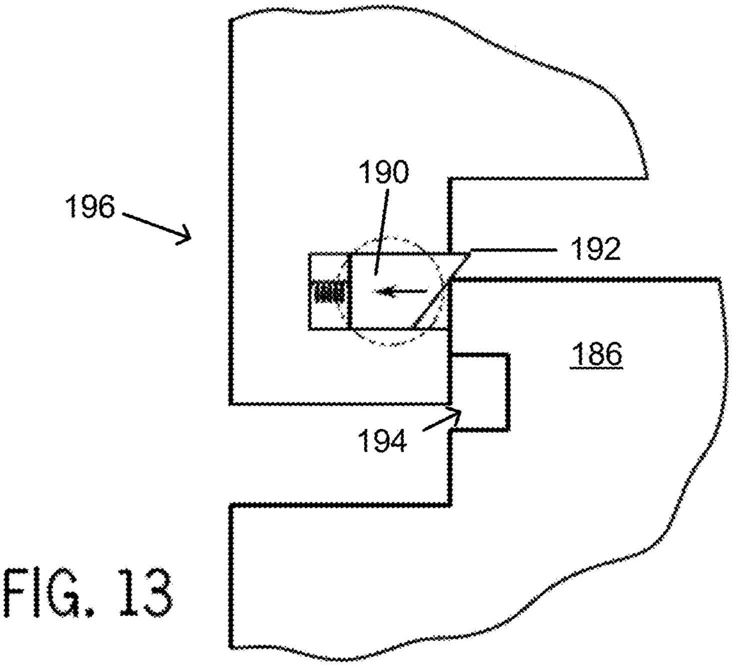
Figure 14:
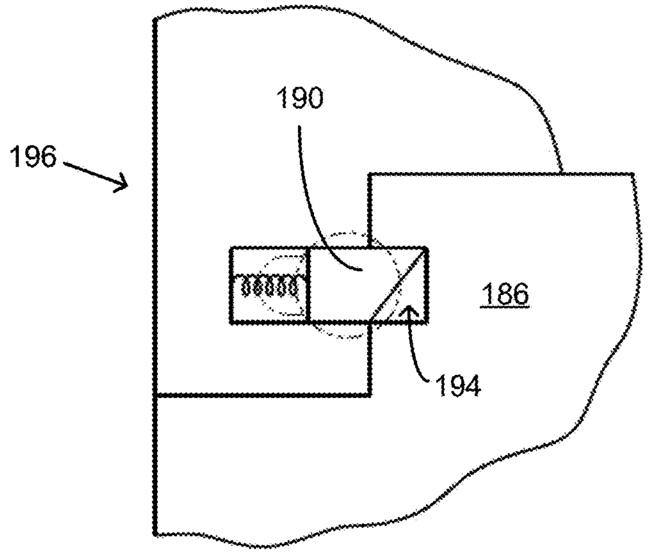

Turning to the attaching and detaching of the respective portions 180, 182 of the rack 100, as seen in FIGS. 10-11, the attachment mechanism 196 includes a female receiving portion 184 on the top portion of the positioning section 128 and a male engaging portion 186 on the bottom portion 182 of the positioning section 128. As seen in FIG. 11, the female receiving portion 184 receives the male engaging portion 186 within a sleeve 188 formed within the female receiving portion 184. Referring to FIGS. 12-14, the female receiving portion 184 includes a pair of spring-loaded tabs 190 on opposite ends of the rack 100 that are biased such that an angular portion 192 of the tabs 190 project into the sleeve 188 when an opposing force is not applied to the tabs 190. The angular portion 192 of the tabs 190 are angled upward and toward a central point of the rack such that when the female receiving portion 184 receives the male engaging portion 186 within the sleeve 188, the tabs 190 are depressed within a tab cavity 194 by the relative upward movement of a top edge 194 of the male engaging surface 186. As the male engaging surface 186 is advanced within the sleeve 188, the tabs 190 spring or lock into place within a cutout formed within the bottom portion of the positioning section 128. Once locked, the tabs 190 are once again positioned with the angular portion 192 of the tabs 190 projecting into the sleeve 188 and into the tab cavity 194 of the bottom portion of the positioning section 128. To disengage the top detachable portion 180 from the bottom detachable portion 182, the tabs 190 may be depressed outward or laterally such that the angular portion 192 of the tabs 190 do not project within the sleeve 188, and the top detachable portion 182 may be lifted vertically until the male engaging portion 186 no longer occupies the sleeve 188 of the female receiving portion 184. While the female receiving portion 184 is described as being positioned on the top detachable portion 180 and the male engaging portion 186 is described as being positioned on the bottom detachable portion 182, the rack 100 can similarly function in an opposite arrangement of the male engaging portion 186 and the female receiving portion 184.

Figure 15:
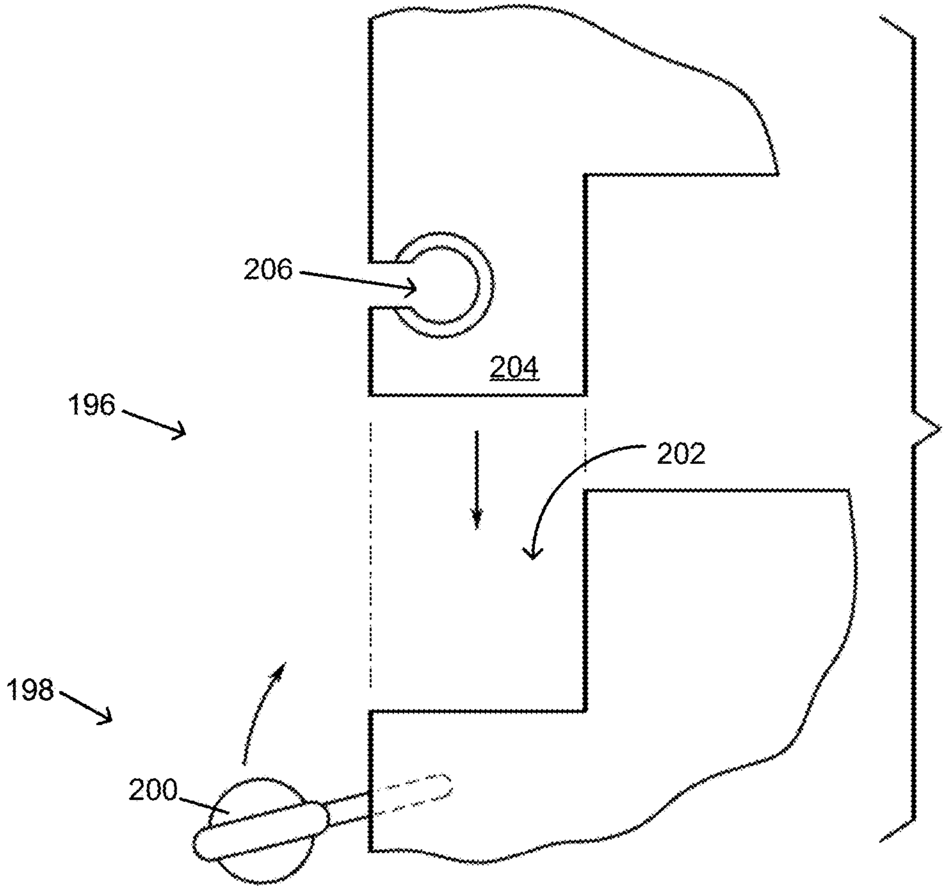
FIGS. 15-16 show a front view of another example of a portion of an attachment mechanism securing the top detachable portion to the bottom detachable portion of the medical rack.
Figure 16:
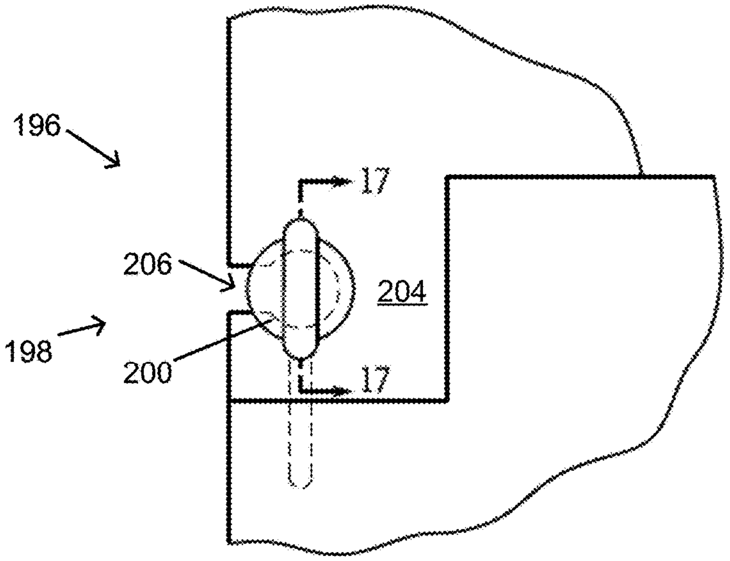
Figure 17:
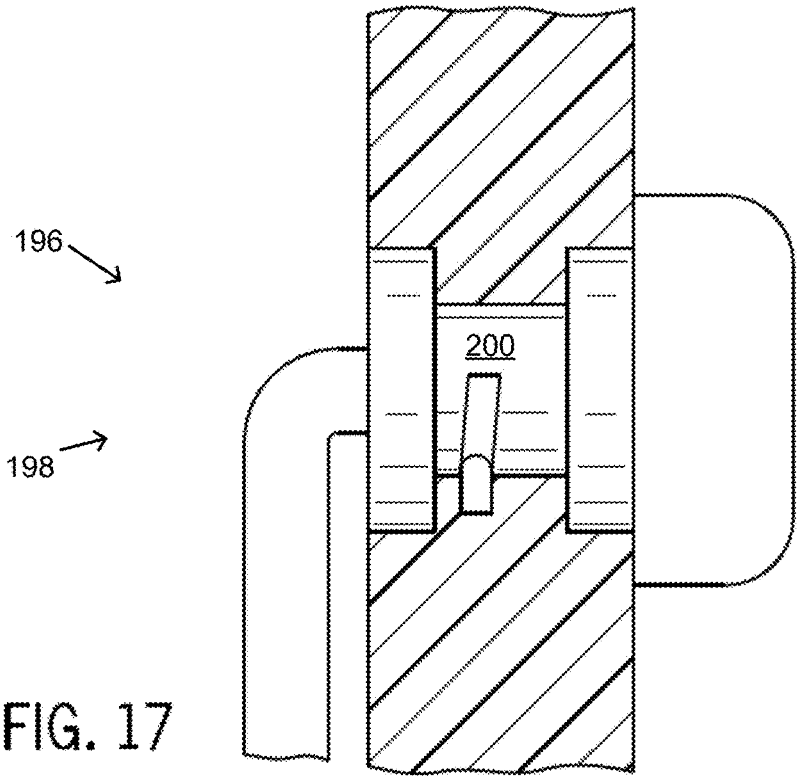
FIG. 17 shows a side view of a knob fastener.

Now referring to other mechanisms to secure the top detachable portion 180 to the bottom detachable portion 182, as seen in FIGS. 15-17, the attachment mechanism 196 includes a pair of knob fasteners 198, such as % turn knob fasteners, on opposing sides of the rack 100. A knob 200 or similar securing mechanism secures the top detachable rack portion 180 to the bottom detachable rack portion 182. As described previously, the top detachable portion 180 may include a female receiving portion 184 forming a sleeve 188 to receive a male engaging portion 186 of the bottom detachable portion 182. The sleeve 188 may stabilize the respective portions 180, 182 of the rack 100 and the knob fastener 198 may secure the portions 180, 182 together. As seen in FIGS. 15-17, the knob 200 is pivotally mounted to the bottom detachable portion 182 and can be manually swung outward and up until it friction-fits within a circular cut out 206 in the top detachable portion 180. To tighten, the knob can be turned % of a turn to fasten and secure the knob 200 within the circular cut out 206. In this embodiment, the bottom detachable portion 180 includes recessed cut outs 202 and the top detachable portion includes corresponding protrusions 204 to fit within the cut outs 202. When the protrusions 204 fit within the cut outs 202, the knob 200 can be manually swung up and into the circular cut outs 206 of the top detachable portion 180 of the rack 100.

Figure 18:
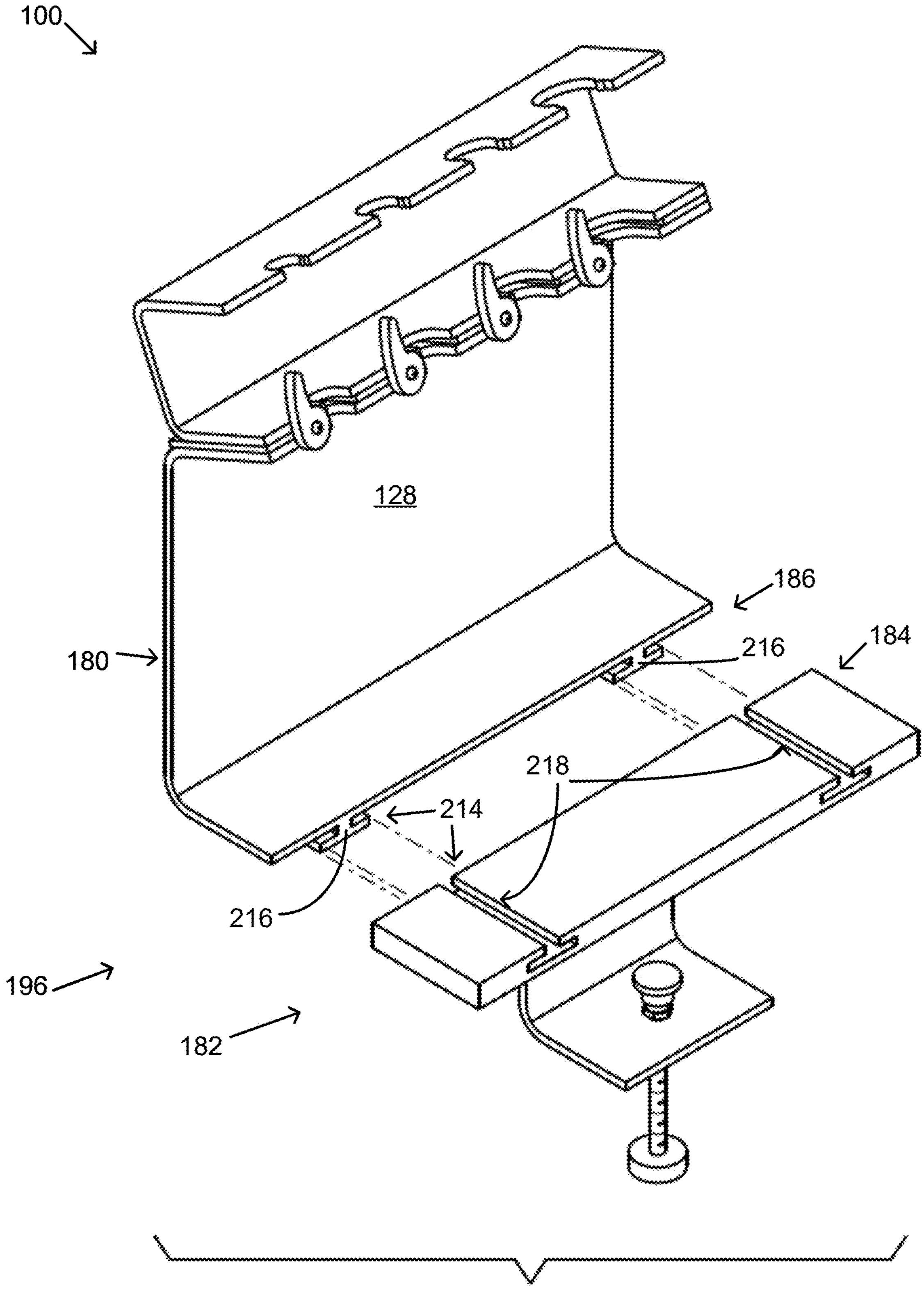
FIGS. 18-21 show example attachment mechanisms between the top detachable portion and the bottom detachable portion of the medical rack.
Figure 19:
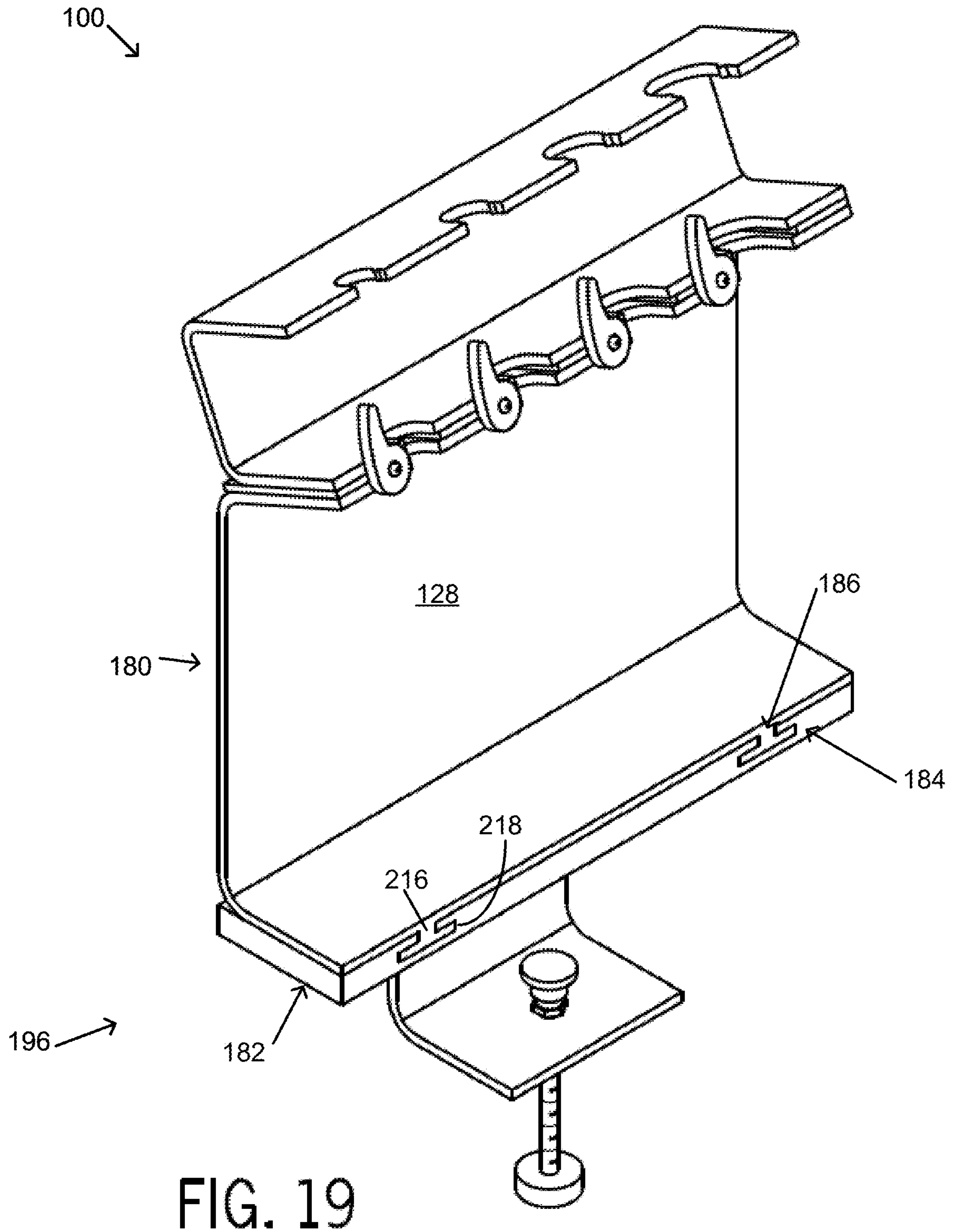

Further mechanisms to secure the top detachable portion 180 to the bottom detachable portion 182, as seen in FIGS. 18-19, can include a medical rack 100 with a male engaging portion 186 and a female receiving portion 184 that define interlocking joints 214 that dovetail together. In particular, the male engaging portion 186 includes an upside down T-shaped projection 216 on the one or more upper securing members 122 that slideingly engages with a corresponding T-shaped cut out 218 on the female receiving portion 184. The interlocking joints 214 are configured such that the male engaging portion 186 may slideingly engage with the female engaging portion 184 such that once latched, the rack 100 will be stable and secure. While the embodiment of FIGS.

18-19 depicts the interlocking joints 214 in a horizontal arrangement relative to the positioning surface 128, the interlocking joints 214 can also be positioned vertically in place of the positioning section 128 or on a portion of the positioning section 128. In either a horizontal or vertical arrangement of the interlocking joints 214, a locking mechanism may be utilized in conjunction with the joints 214 that is similar to as described in other parts of the disclosure.

Figure 20:
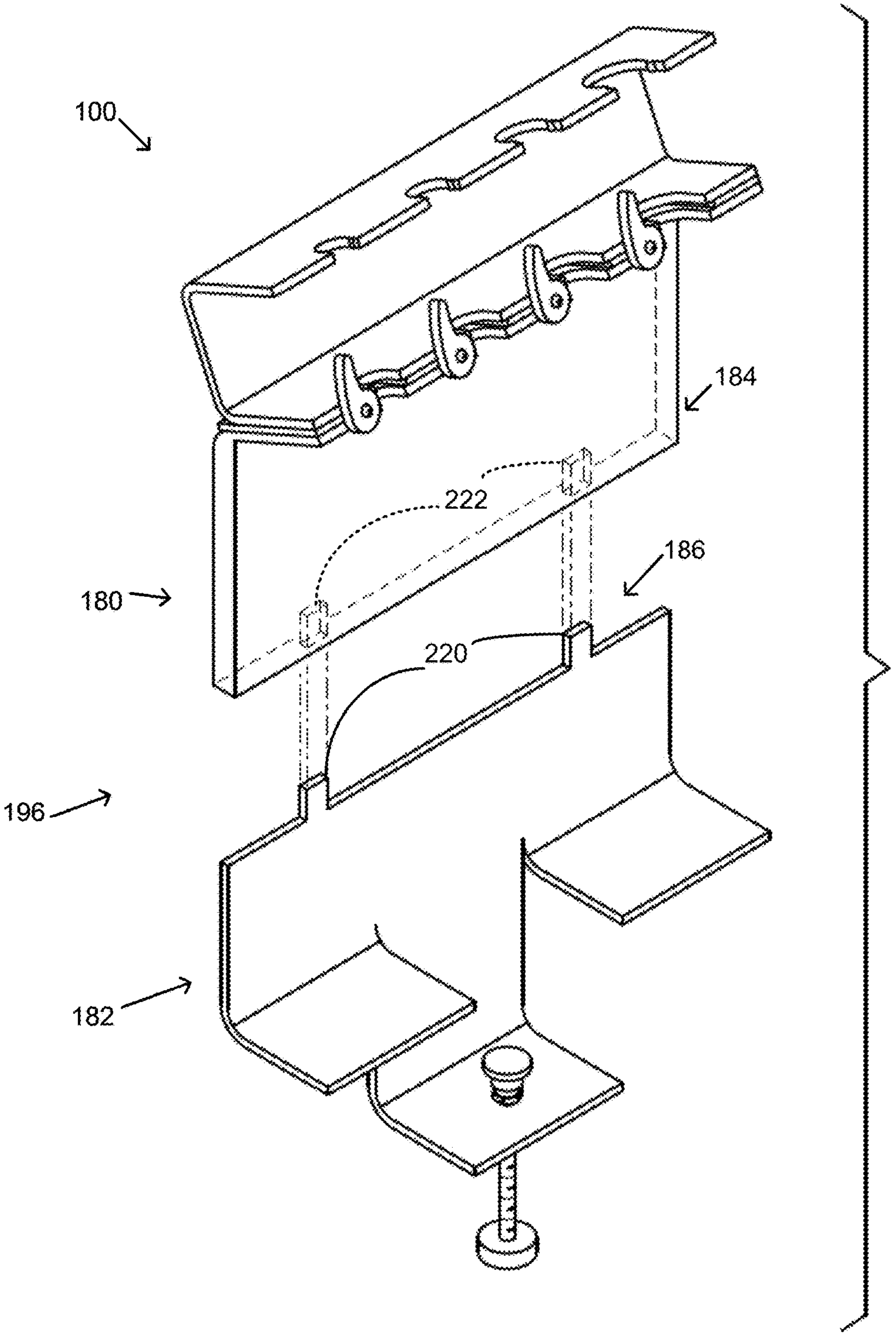
Figure 21:
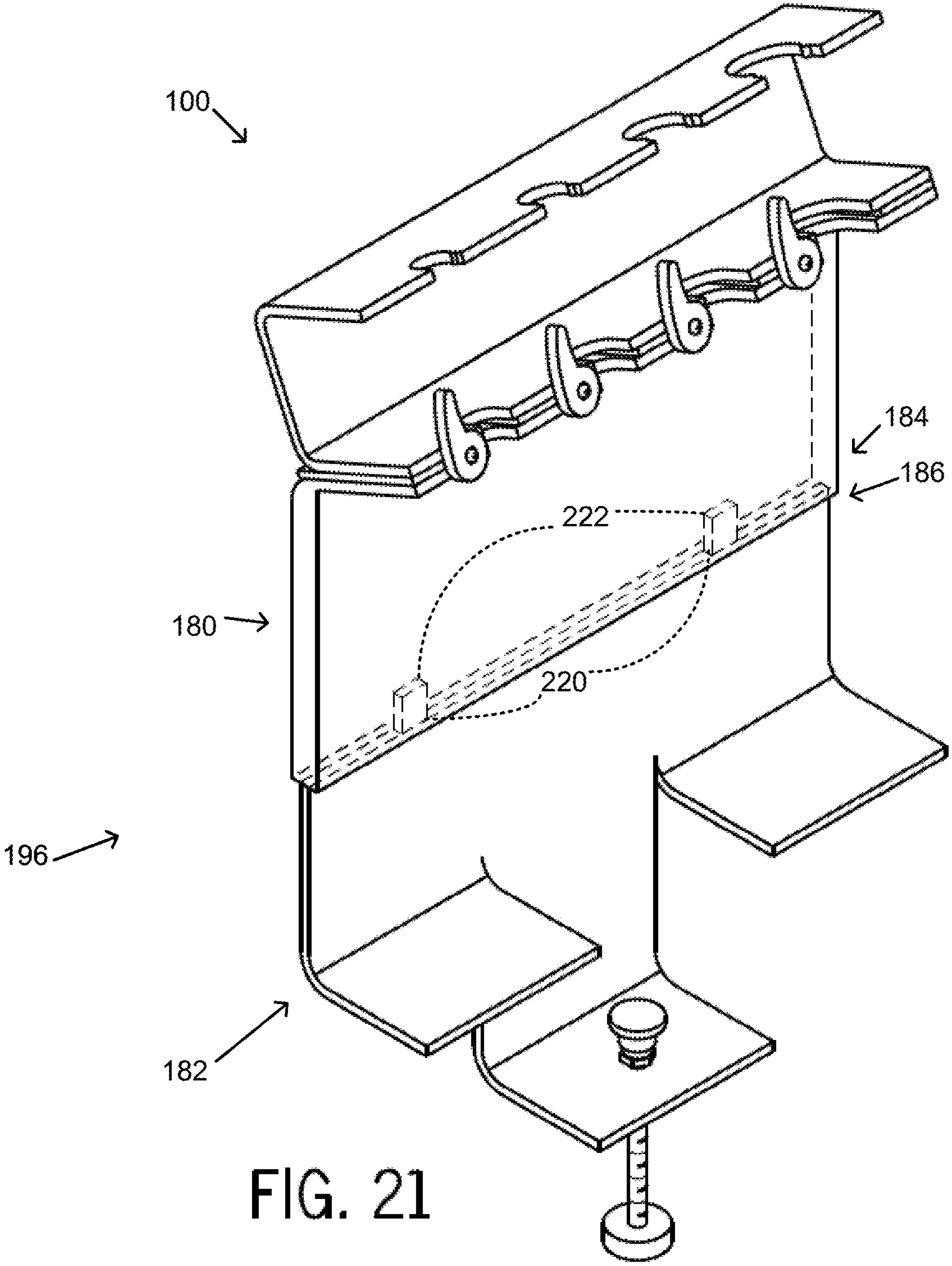

Another mechanism to secure the detachable rack 100 may include a male engaging portion 186 that includes tabs 220 that friction-fit within a cavity 222 formed within a female receiving portion 184, as seen in FIGS. 20-21. The male engaging portion includes two tabs 220 on an upper edge of the positioning section 128 on the bottom detachable portion of the rack 100. The tab cavities 222 are formed within the positioning section 128, which, in this particular embodiment is thicker than other embodiments. The rack 100 may additionally include a securing or locking mechanism (not shown) so secure the rack 100 together when the tabs 220 are frictionally engaged with the tab cavity 222. For example, an inner portion of the tab cavity 222 may include a ferrous metal and the tab 220 may include a magnet, or vice versa. As another example, a spring-loaded tab 190 may be added to the embodiment of FIGS. 20-21 in order to further secure the top detachable portion 180 to the bottom detachable portion 182.

Other attachment mechanisms 196 are possible to secure the top detachable portion 180 of the rack 100 to the bottom detachable portion 182. For example, the detachable rack 100 may include a bottom detachable portion 182 that includes a laterally extending positioning section 128, similar to that as described with reference to FIG. 10. The positioning section 128 of the presently described embodiment, however, differs from the embodiment in FIG. 10 in that it includes a T-shaped member (not shown) having an upper bar extending orthogonal to a bottom, vertical bar that is centrally positioned and extending upward from the positioning section 128. The T-shaped member may engage with and be received within a sleeve 188 of the female receiving portion 184 of the top portion 180 of the rack 100. The female receiving portion 184 may include spring-loaded clasps (not shown) that are biased inward. The spring-loaded clasps may include angled tips that can receive and firmly secure around the upper bar of the T-shaped member, thus, securing the top portion 180 to the bottom portion 182. As the T-shaped member slides into the sleeve 188 of the female receiving portion 184, the upper bar pushes the clasp horizontally until the upper bar passes the angled tips of the clasp. At this point, once the base is fully inserted into the sleeve, the clasp will snap in place on both sides of the T-shaped member. The female receiving portion may further include an elongated push rod that is positioned between the clasps such that is will compress when the T-shaped member engages between the clasps. The elongated push rod may be spring-biased such that it pushes against the top bar of the T-shaped member. To disengage the clasps from the T-shaped member, a thumb tab on the outside of the disposable rack 100 will slide upward, away from the base, releasing the clasps from the T-shaped member and releasing the elongated rod to separate the detachable rack form the base for easy removal.

In certain embodiments, the medical rack 100 may include an attachment mechanism 196 that includes a pin that is inserted into a receiving portion, such as a hole, that goes through both the male engaging portion 186 and the female receiving portion 184, a tab that is attached to the disposable top and the base and a has a hole that matches up for a pin to be inserted through it, or the like, and will securely fasten the device together. The pins/clips can be adapted and modified to fit any specific design. This includes but is not limited to hitch pins/clips, lynch pins, quick release pins, grooved pin/clip, spring pin, taper pin, cotter pin, etc.

In addition to the attachment mechanisms 196 described herein, the attachment mechanisms 196 may be adapted and modified to fit any specific medical rack design. For example, where laches, clasps, and spring loaded tabs are described, the mechanisms may also or alternatively include other mechanisms such as an actus rubber latch, T-latch, over center draw latch, swing latch, rotomold replacement latch, spring latch, twist latch, under center draw latch, bolt, compression latch, spring latch, thermoplastic latch, draw latch, latch push/pull toggle clamp, etc.

Figure 23:
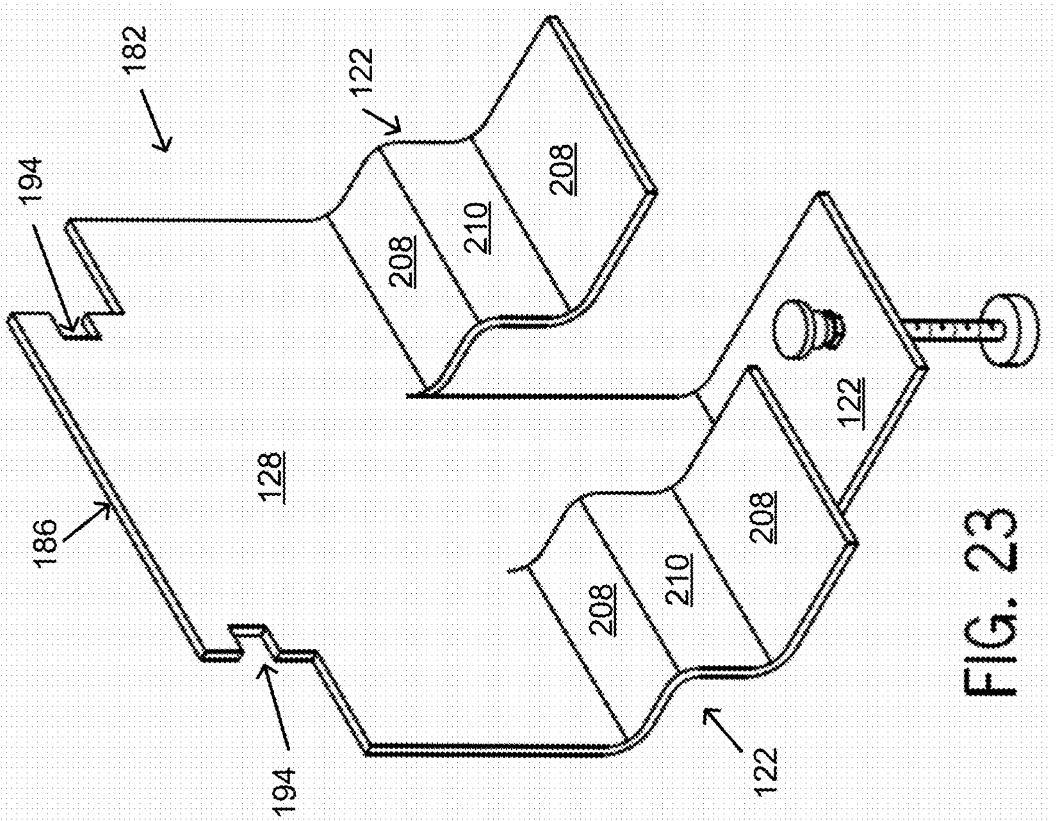
FIGS. 22-24 show isometric front views of example securing portions of the medical rack.
Figure 22:
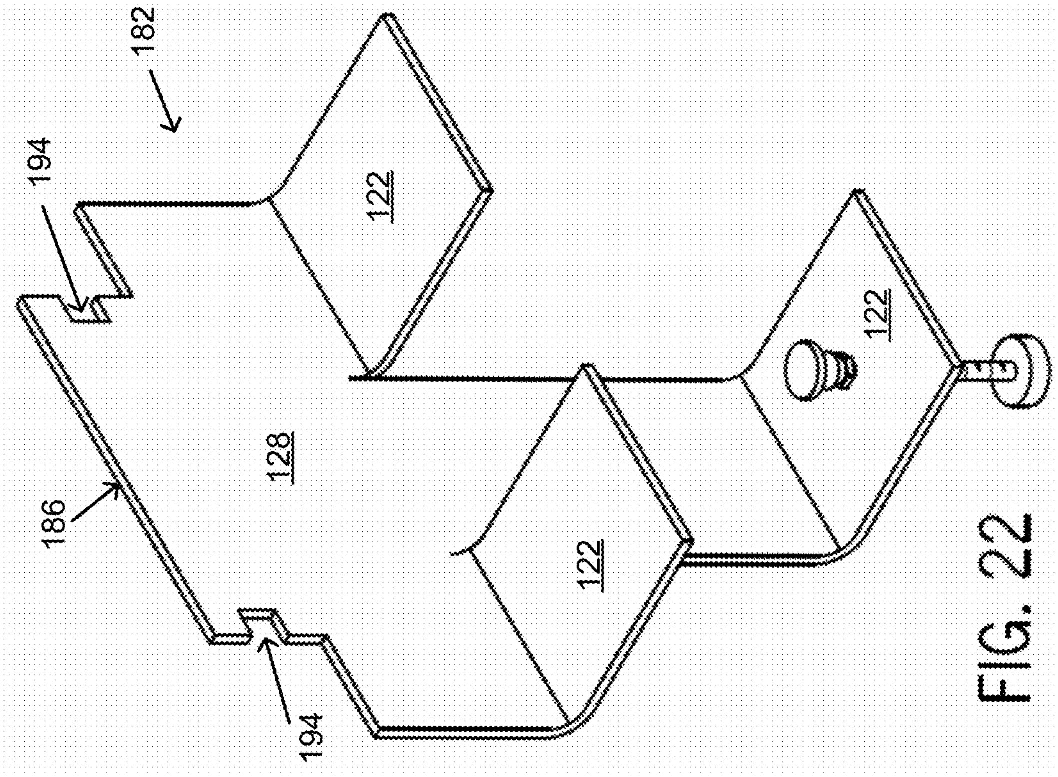
Figure 24:
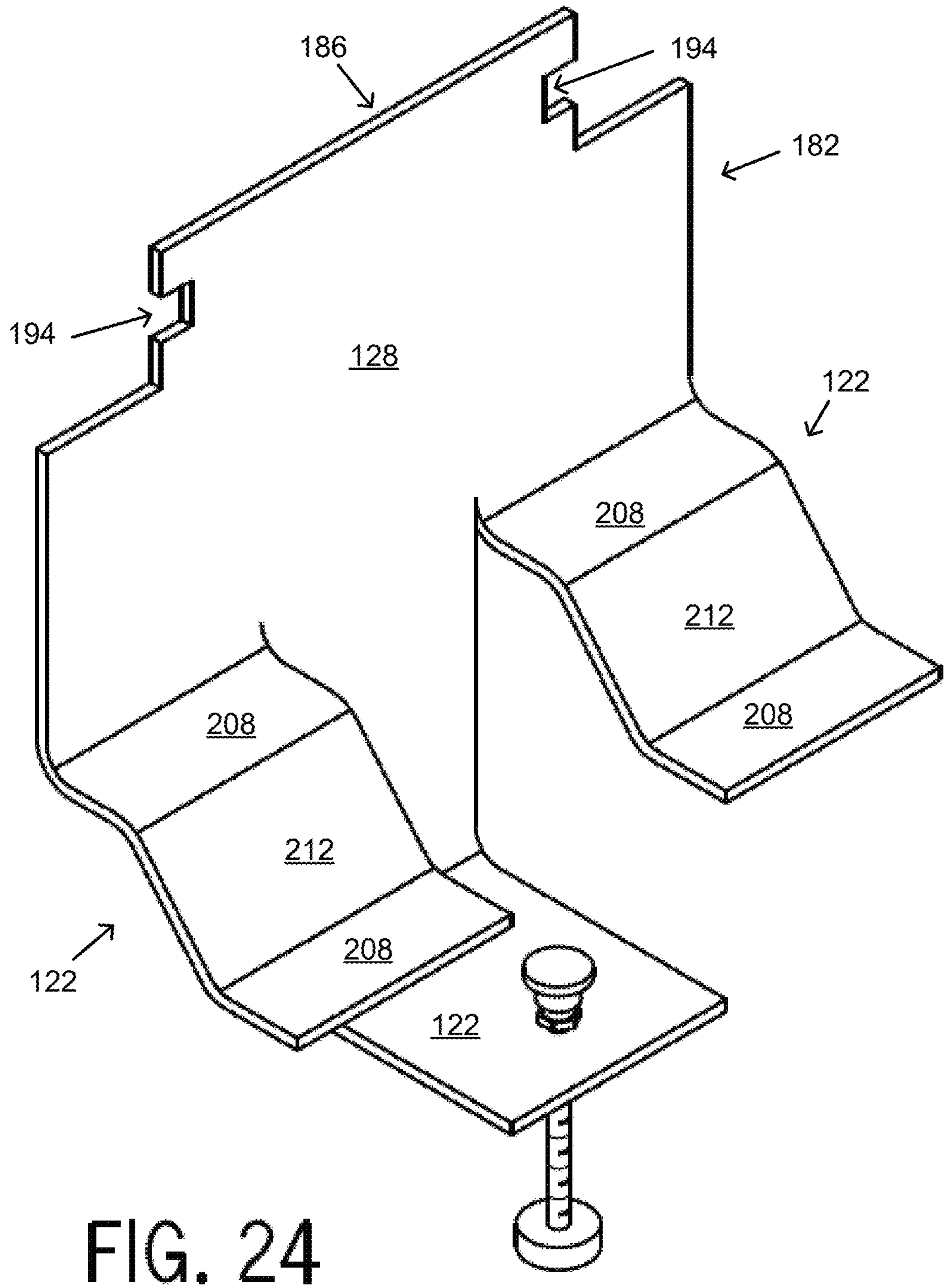

The detachable rack 100 may include alternative securing members 122 on the securing portion 120 of the rack. As seen in FIGS. 22-24, the one or more surfaces are configured to fit any number of fixtures 124. FIG. 22, for example, includes two members 122 that are planar and generally perpendicular to the positioning section 128. The members 122 of this embodiment may secure the rack 100 to surfaces that include flat surfaces, such as a table with flat or square edges. FIG. 23, for example, includes two members 122, where each defines a stair step pattern with two horizontal sections 208 and a vertical section 210 between the horizontal sections 208. These surfaces 122 are configured to fit, for example, an operating room table with a stair step pattern along the edge of the fixture 124. FIG. 24, for example, includes two members 122, where each defines an angled stair step pattern with two horizontal sections 208 and a vertically descending section 212 between the horizontal sections 208. These surfaces 122 are configured to fit, for example, a "MAYO" table with an angled stair step patter along the edge of the fixture 124.

Figure 25:
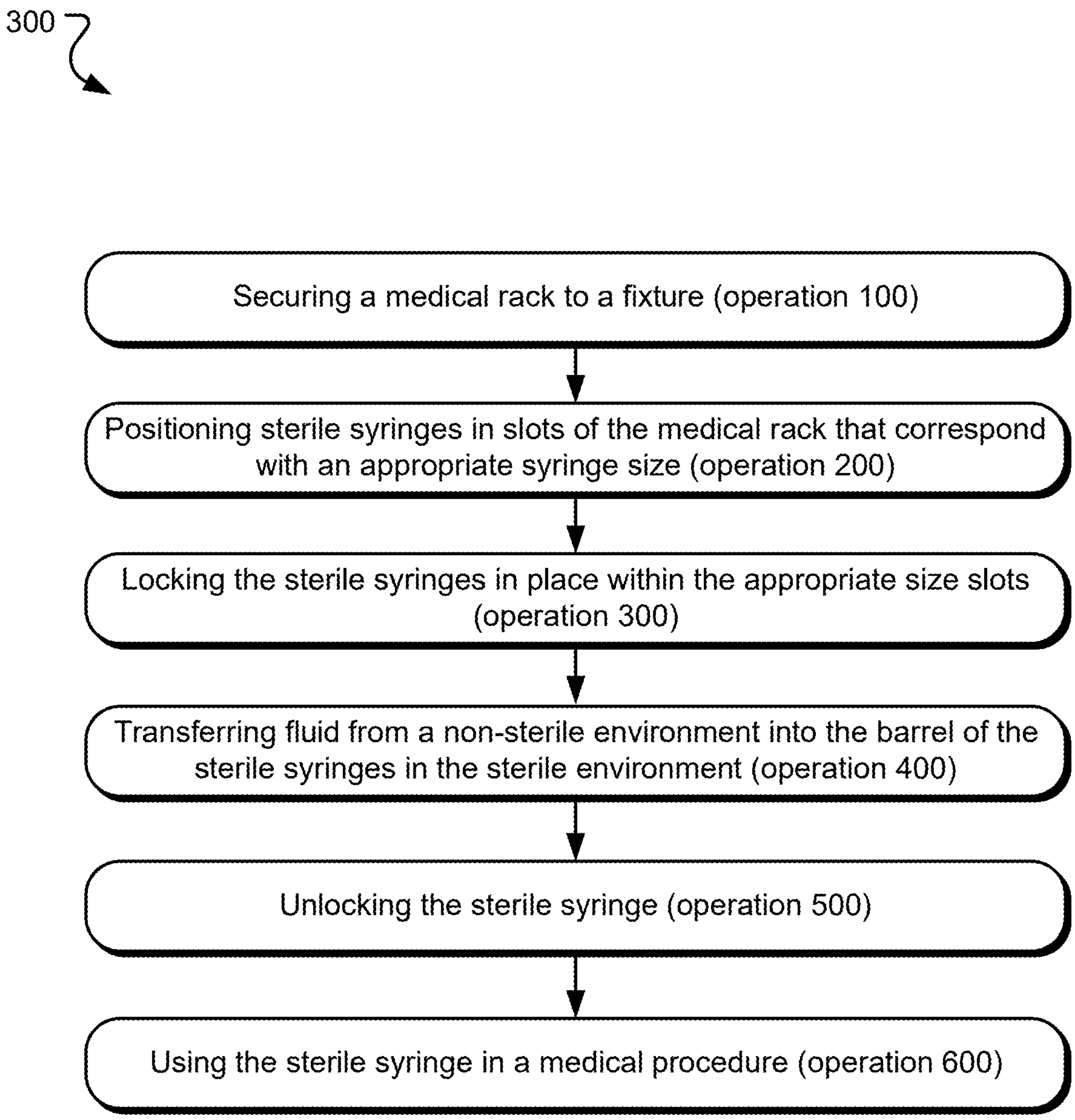
FIG. 25 is a flowchart showing an example method of a sterile transfer of fluid.

Referring to FIG. 25, a method 300 of sterile transfer of the fluid can include the following steps. Securing a medical rack to a fixture (operation 100). Positioning sterile syringes 100 in respective syringe-receiving stations 166 of the medical rack 100 that correspond with an appropriate syringe size (operation 200). Positioning may entail snapping the barrel 112 of the syringe 110 into a syringe-receiving station 166 such that an upper syringe-receiving recess 170 receives the syringe barrel 112 near the distal end of the syringe 110, and a corresponding lower syringe-receiving space 146 receives the syringe barrel 112 and syringe tab(s) 111 near the proximal region of the syringe 110. The positioning step may also entail orienting the opening 114 in the barrel 112 of the syringe 110 away from the fixture 124 at an angle that facilitates convenient loading of the syringes 110 with fluid by a medical professional that is adjacent the fixture 124. The positioning step may additionally entail coupling the distal ends of the syringes 110 with butterfly tips 116. The butterfly tips 116, however, may be coupled to the syringes 110 prior to positioning the syringes 110 on the rack 100.

Moving on, the method 300 of sterile transfer of fluid further includes locking the sterile syringes in place within the appropriate stations 166 (operation 300). This step may entail rotationally engaging a lock to securely support the tab 111 of a syringe 110. Next, the method may involve transferring or loading fluid from a non-sterile environment into the barrel of the sterile syringes (operation 400). Transferring the fluid may entail loading a non-sterile syringe with fluid from a vial or other container and removing a needle at the distal end of the non-sterile syringe. The needleless distal end of the non-sterile syringe is then frictionally engaged with the unoccupied port 115 on the butterfly tip 116, and the fluid is transferred from the non-sterile syringe, through the butterfly tip 116, and into the sterile syringe 110. At this point, the non-sterile syringe and the butterfly tip 116 can be de-coupled with the sterile syringe 110. Transferring the fluid may alternatively entail threading a needle from a non-sterile syringe into an opening of the sterile syringe and dispensing the fluid from the non-sterile syringe into the barrel of the sterile syringe. Alternatively, transferring the fluid may entail threading a needle from a sterile syringe into an opening of a non-sterile syringe, vial, or container and dispensing the fluid from the non-sterile syringe, vial, or container into the barrel of the sterile syringe.

The method 300 may additionally entail unlocking the loaded or filled sterile syringes (operation 500) and using the sterile syringe in a medical procedure (operation 600). If the medical rack is detachable, an additional step may entail transferring a top portion of the detachable rack to a bottom portion of the rack (operation 700). This step may occur before or after fluid is dispensed into the sterile syringes. For example, the fluid may be transferred into the sterile syringes while the top portion of the detachable rack is coupled with a first bottom portion of a rack, and the top portion of the detachable rack may be transferred to a second bottom portion of a rack where the sterile syringes will be used in a medical procedure. As another example, the unfilled sterile syringes may be secured in a top portion of a rack that is docked to a first bottom portion of a rack. The loaded and unfilled syringes may then be transferred to a second bottom portion of a rack where fluid will be dispensed into the unfilled sterile syringes and used in the medical procedure.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular embodiments. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A device for holding a syringe, the device comprising:

a syringe receiving portion including a lower planar surface forming a bottom region of the syringe receiving portion, the lower planar surface extending at an angle from an adjoining planar surface of the syringe receiving portion; and a securing portion including an upper planar surface to form a parallel attachment with the lower planar surface of the syringe receiving portion, the securing portion including one or more upper rack securing surfaces extending from a bottom region of the securing portion, the upper planar surface of the securing portion positioned non-parallel with the one or more upper rack securing surfaces.

2. The device of claim 1, wherein:

the lower planar surface of the syringe receiving portion forms an upper syringe engaging member; and the upper planar surface of the securing portion forms a lower syringe engaging member.

3. The device of claim 1, wherein the securing portion is formed as a single piece of metal.

4. The device of claim 1, wherein the syringe receiving portion is formed as a single piece of metal.

5. The device of claim 1, wherein:

the securing portion further includes:

a lower rack securing surface, beneath the one or more upper rack securing surfaces, and extending from a planar midsection of the securing portion.

6. The device of claim 5, wherein an upper planar portion forming an upper region of the syringe receiving portion is non-parallel with the one or more upper rack securing surfaces or the lower rack securing surface.

7. The device of claim 5, wherein the lower planar surface forming the bottom region of the syringe receiving portion is non-parallel with the one or more upper rack securing surfaces or the lower rack securing surface.

8. The device of claim 5, wherein the upper planar surface of the securing portion is non-parallel with the lower rack securing surface.

9. The device of claim 1, further comprising an intermediate spacing portion between the lower planar surface and the upper planar surface, the intermediate spacing portion forming a slot to receive a portion of the syringe.

10. The device of claim 1, wherein the upper planar surface of the securing portion forms a non-perpendicular angle with an extended planar section of the securing portion.

* * * * *